US008703732B2

(12) United States Patent
Kim et al.

(10) Patent No.: US 8,703,732 B2
(45) Date of Patent: Apr. 22, 2014

(54) COMPOSITION FOR ENHANCING TRAIL SENSITIVITY COMPRISING INHIBITORS FOR EXPRESSION OR ACTIVITY OF TIP41 AS A TARGET GENE OF TRAIL SENSITIZER

(75) Inventors: Nam-Soon Kim, Daejeon (KR); In-Sung Song, Daejeon (KR); Cheol-Hee Kim, Daejeon (KR); Ga Hee Ha, Daejeon (KR); Hyun-Taek Kim, Daejeon (KR); So-Young Jeong, Daejeon (KR); Jeong-Min Kim, Daejeon (KR); Joo Heon Kim, Daejeon (KR); Jin-Man Kim, Daejeon (KR); Soo Young Jun, Daegu (KR)

(73) Assignee: Korea Research Institute of Bioscience and Biotech, Daejeon (KR)

( * ) Notice: Subject to any disclaimer, the term of this patent is extended or adjusted under 35 U.S.C. 154(b) by 0 days.

(21) Appl. No.: 13/579,256

(22) PCT Filed: Apr. 1, 2011

(86) PCT No.: PCT/KR2011/002300
§ 371 (c)(1),
(2), (4) Date: Aug. 15, 2012

(87) PCT Pub. No.: WO2011/122916
PCT Pub. Date: Oct. 6, 2011

(65) Prior Publication Data
US 2012/0315284 A1 Dec. 13, 2012

(30) Foreign Application Priority Data

Apr. 1, 2010 (KR) ........................ 10-2010-0030004

(51) Int. Cl.
C12N 15/11 (2006.01)
A61K 48/00 (2006.01)
C07H 21/02 (2006.01)
C07H 21/04 (2006.01)

(52) U.S. Cl.
USPC ........................ 514/44 A; 536/24.5

(58) Field of Classification Search
USPC .................. 514/44; 536/23.1, 24.5
See application file for complete search history.

(56) References Cited

U.S. PATENT DOCUMENTS 7,217,797 B2 5/2007 Hinton et al.
7,217,798 B2 5/2007 Hinton et al.
(Continued)

FOREIGN PATENT DOCUMENTS

JP 2007-531707 A 11/2007
WO 2004035752 A2 4/2004
(Continued)

OTHER PUBLICATIONS

Song et al. (Gastroenterology, 2012 vol. 143, No. 5, pp. 1341-1351).*
(Continued)

Primary Examiner — Terra Cotta Gibbs
(74) Attorney, Agent, or Firm — Lando & Anastasi LLP

(57) ABSTRACT

The present invention relates to a pharmaceutical composition, including inhibitors for expression or activity of TIP41 protein, for prevention and treatment of cancer. When the liver cancer cell lines, showing resistance to TRAIL, are treated with TIP41 siRNA and TRAIL, apoptosis is induced in cancer cell. The same effect is found in cases of lung cancer and colon cancer with resistance against TRAIL. Moreover, this induction of apoptosis by TIP41 siRNA and TRAIL was confirmed in tumor xenograft, which was injected with Huh7 liver cancer cells and then was subjected to TIP41 siRNA transfection and TRAIL treatment. In addition, it was confirmed through animal experiments in which the tumor size has reduced and apoptosis was induced by treatment with TIP41 siRNA and TRAIL. Of note, MKK7/JNK pathway was confirmed to mediate the apoptosis induced by the application of TIP41 siRNA and TRAIL. The apoptosis were verified to be caused by the activation of MKK7/JNK signaling pathway. Taken together, the present invention provide the strong evidence that the pharmaceutical composition, including inhibitors for TIP41 expression or activity can be used for cancer prevention and treatment as well as an anti-cancer adjuvant. Taken together, the pharmaceutical composition comprising inhibitors for expression or activity of TIP41 protein may be used for prevention and treatment of cancer or as an anti-cancer adjuvant.

11 Claims, 18 Drawing Sheets

(56) References Cited

U.S. PATENT DOCUMENTS

| | | |
|---|---|---|
| 7,361,740 B2 | 4/2008 | Hinton et al. |
| 7,365,168 B2 | 4/2008 | Hinton et al. |
| 7,732,570 B2 | 6/2010 | Hinton et al. |
| 8,017,118 B2 | 9/2011 | Nakamura et al. |
| 2005/0014934 A1 | 1/2005 | Hinton et al. |
| 2005/0032114 A1 | 2/2005 | Hinton et al. |
| 2005/0226864 A1 | 10/2005 | Hinton et al. |
| 2005/0276799 A1 | 12/2005 | Hinton et al. |
| 2008/0287657 A1 | 11/2008 | Hinton et al. |
| 2009/0299038 A1 | 12/2009 | Nakamura et al. |
| 2011/0183412 A1 | 7/2011 | Hinton et al. |

FOREIGN PATENT DOCUMENTS

| | | |
|---|---|---|
| WO | 2004092219 A2 | 10/2004 |
| WO | 2005-037867 A1 | 4/2005 |
| WO | 2005123780 A2 | 12/2005 |
| WO | 2009-116670 A1 | 1/2009 |

OTHER PUBLICATIONS

Chawla-Sarkar et al., Downregulation of Bcl-2, FLIP or IAPs (XIAP and survivin) by siRNAs sensitizes resistant melanoma cells to Apo2L/TRAIL-induced apoptosis, Cell Death and Differentiation (2004) 11, 915-923.

Zangemeister-Wittke, Antisense to Apoptosis Inhibitors Facilitates Chemotherapy and TRAIL-Induced Death Signaling, Ann. N.Y. Acad. Sci. 1002:90-94 (2003).

Xu et al., Sp1-Mediated TRAIL Induction in Chemosensitization, Cancer Res 2008; 68:(16), Aug. 15, 2008.

Chen et al., Induction of death receptor 5 and suppression of survivin contribute to sensitization of TRAIL-induced cytotoxicity by quercetin in non-small cell lung cancer cells, Carcinogenesis, vol. 28, No. 10, pp. 2114-2121, 2007.

Gillespie et al., Bim plays a crucial role in synergistic induction of apoptosis by the histone deacetylase inhibitor SBHA and TRAIL in melanoma cells, Apoptosis (2006) 11:2251-2265.

Liu, et al., The Proteasome Inhibitor PS-341 (Bortezomib) Up-Regulates DR5 Expression Leading to Induction of Apoptosis and Enhancement of TRAIL-Induced Apoptosis Despite Up-Regulation of c-FLIP and Survivin Expression in Human NSCLC Cells, Cancer Res 2007; 67:(10). May 15, 2007.

Junttila, et al., Phosphatase-mediated crosstalk between MAPK signaling pathways in the regulation of cell survival, FASEB Journal, vol. 22 Apr. 2008, 954-965.

Wang, et al., Ectodomain shedding of preadipocyte factor 1 (Pref-1) by tumor necrosis factor alpha converting enzyme (TACE) and inhibition of adipocyte differentiation. Mol Cell Biol. Jul. 2006;26(14):5421-35.

* cited by examiner

Fig. 1

A. Identification of protein expression increase in liver cancer clinical tissue (IHC Method)

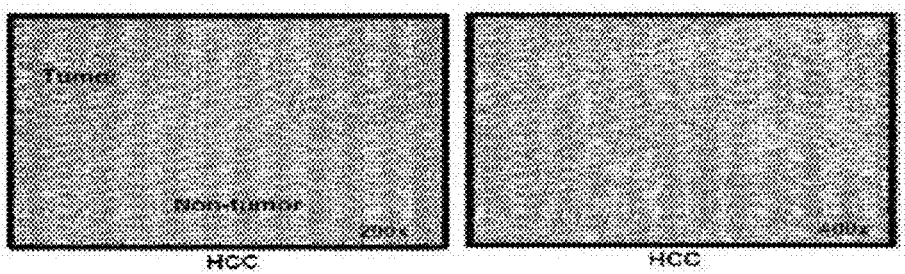

B. Identification of protein expression increase in liver cancer clinical tissue (Western Blot Method)

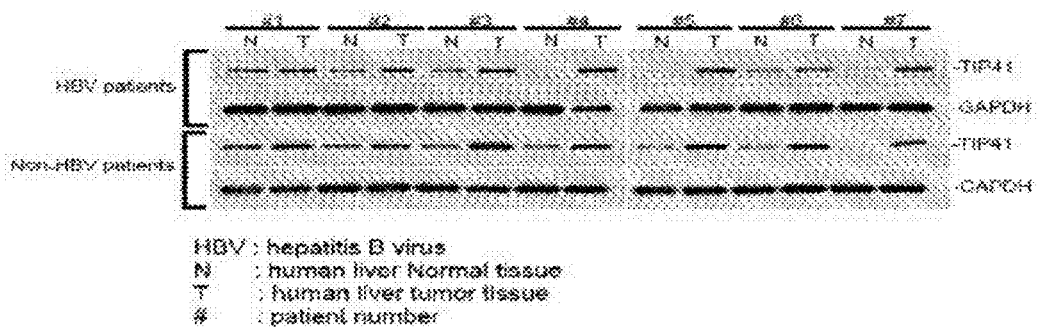

HBV : hepatitis B virus
N : human liver Normal tissue
T : human liver tumor tissue
# : patient number C. Identification of repression of TIP41 protein expression by siRNA (Western Blot Method)

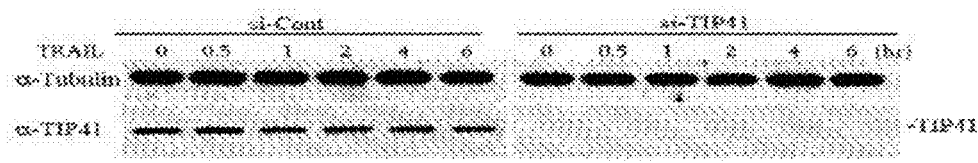

Fig. 2

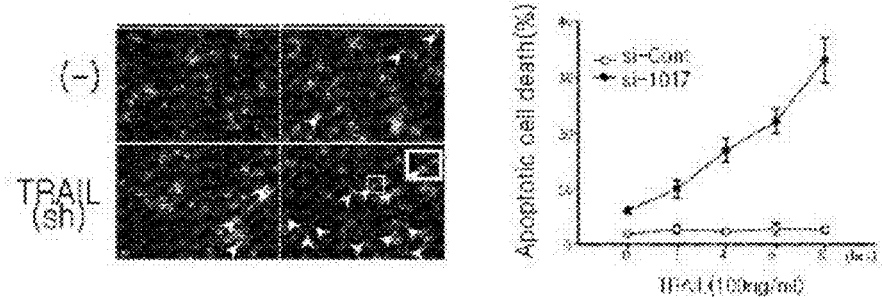

A. TIP41 repression and liver cancer cell line apoptosis from TRAIL treatment- TRAIL treatment in various time periods (Fluorescence microscope analysis with nuclear staining- heochst33342 dye was used)

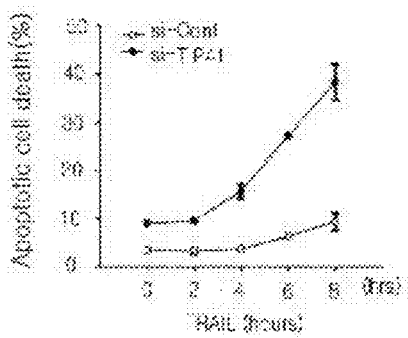

B. TIP41 repression and liver cancer cell line apoptosis from TRAIL treatment- TRAIL treatment in various time periods (FACS analysis method with Annexin V-FITC/PI Staining method was used)

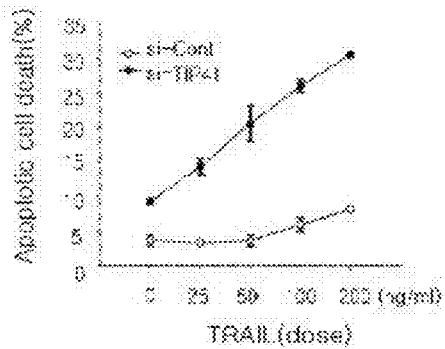

C. TIP41 repression and liver cancer cell line apoptosis from TRAIL treatment- TRAIL treatment in various TRAIL concentrations (FACS analysis method with Annexin V-FITC/PI Staining method was used)

Fig. 3
A. Activation of Caspase cascade
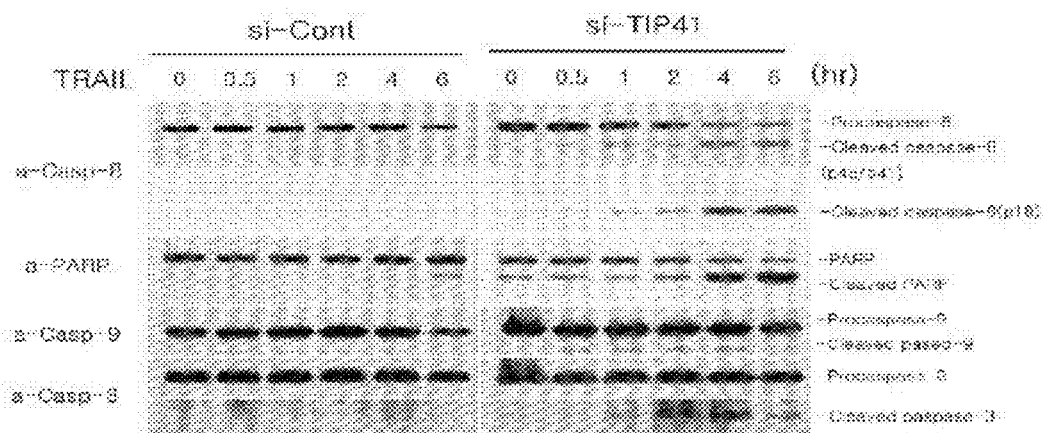
B. Mitochondrial-cytochrome C release
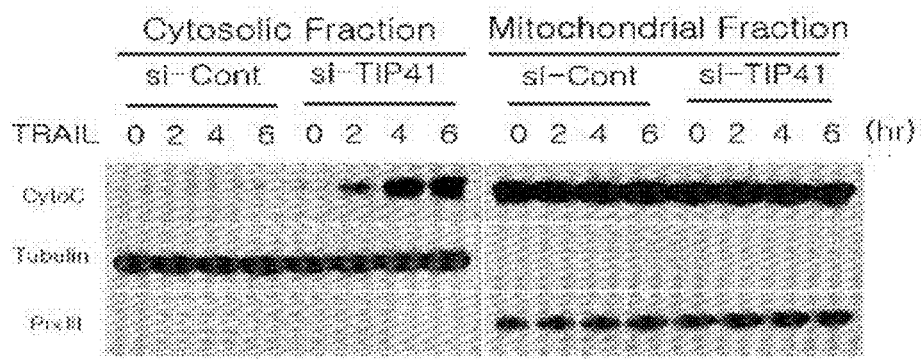

Fig. 4
A. Activation of JNK by TIP41 repression
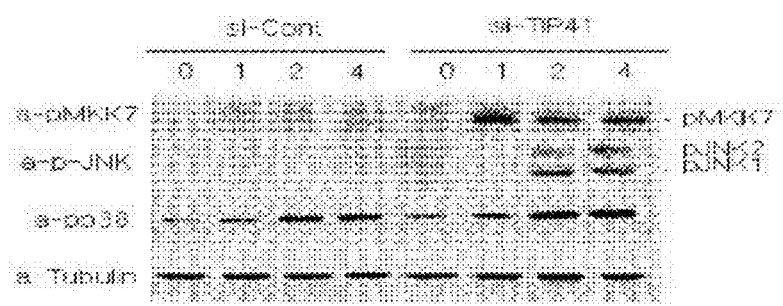
B. Reduction of apoptosis by JNK inhibitor
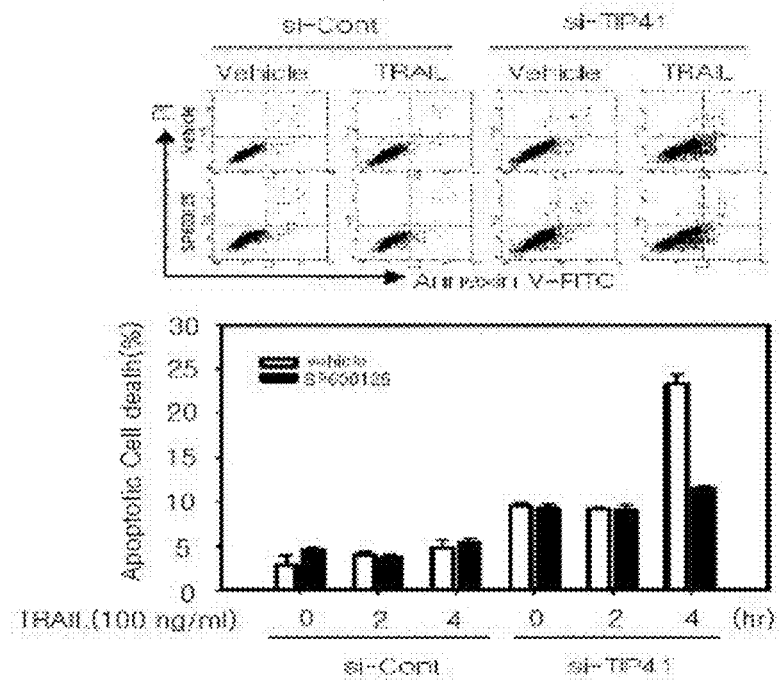

Fig. 5
A. p53-independent apoptosis by TIP41 depletion
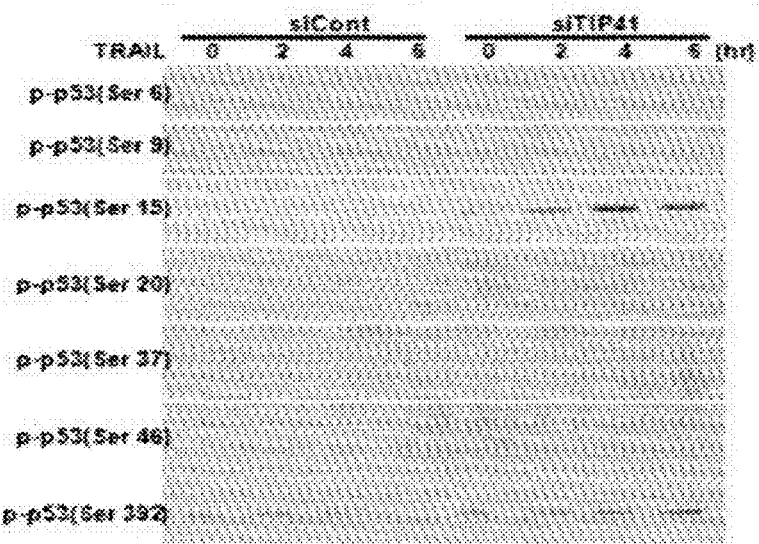
B. Apoptosis using p53-null cell
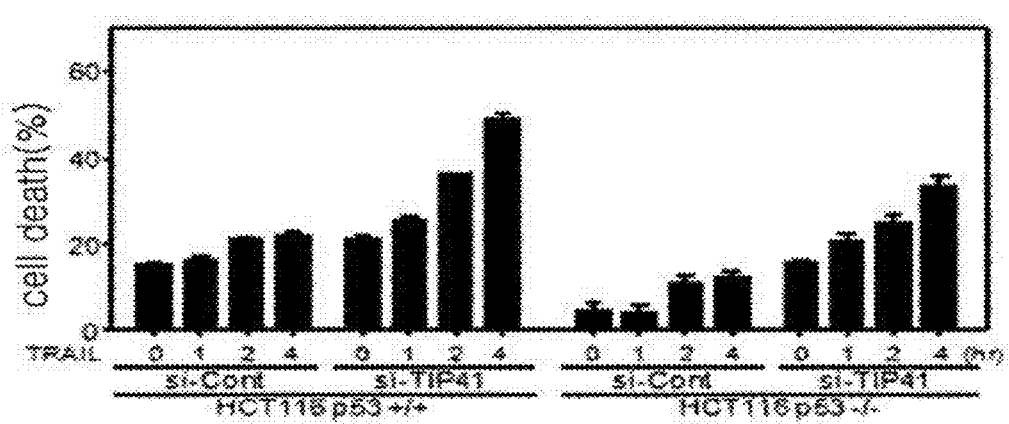

Fig. 6
A. Identification of TRAIL receptor expression for each cell line
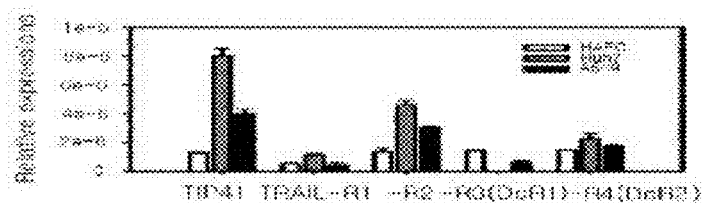
B. Identification of TRAIL receptor expression by TIP repression and TRAIL treatment
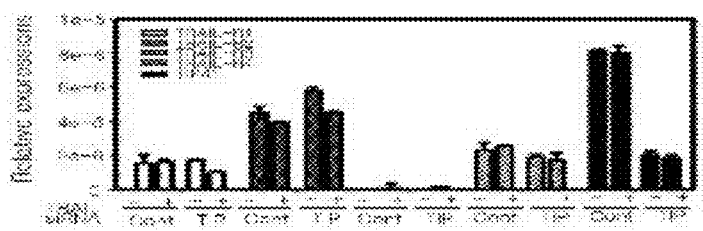
C. Identification of TRAIL receptor expression for each liver cancer clinical tissue
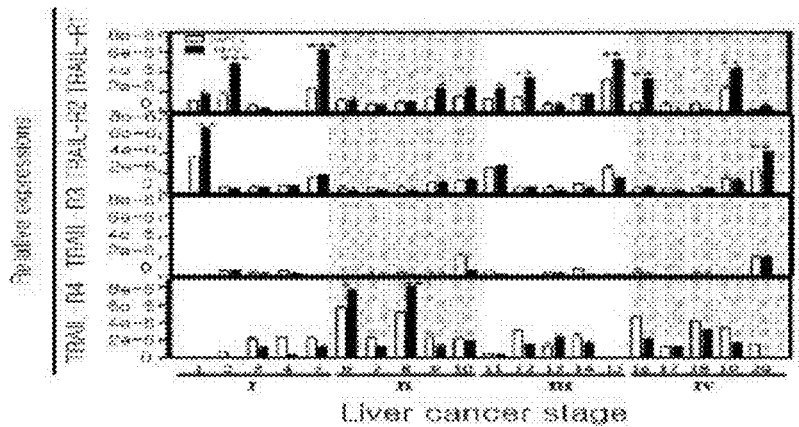

Fig. 7
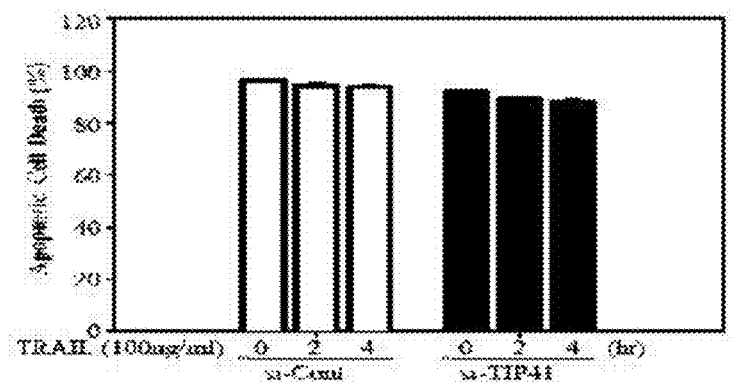
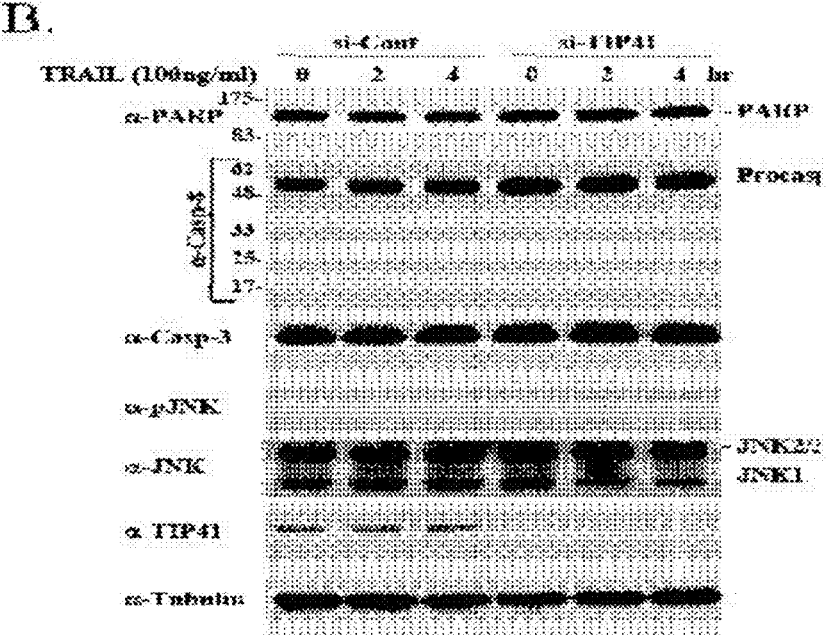

Fig. 8a
A. Lung cancer-A549
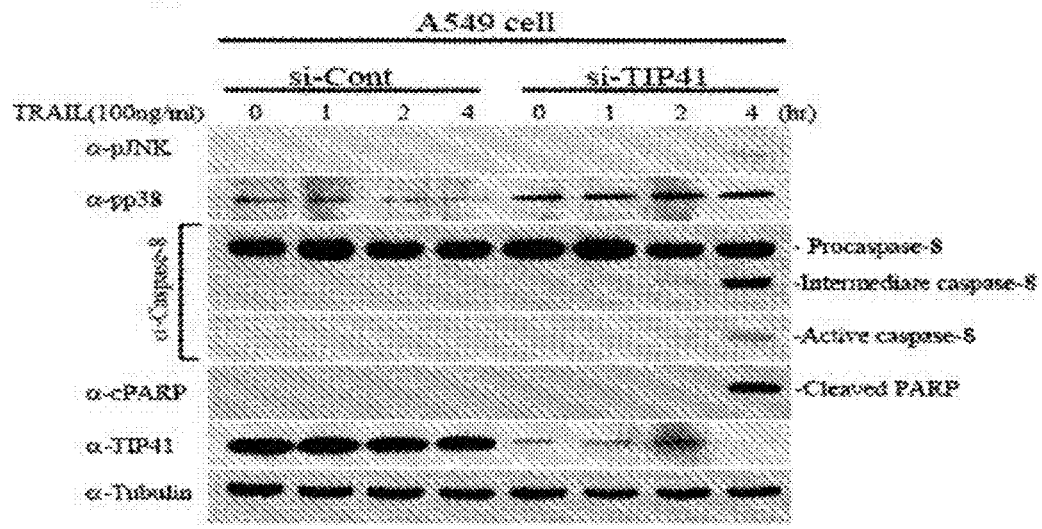
B. Colon cancer - HCT116
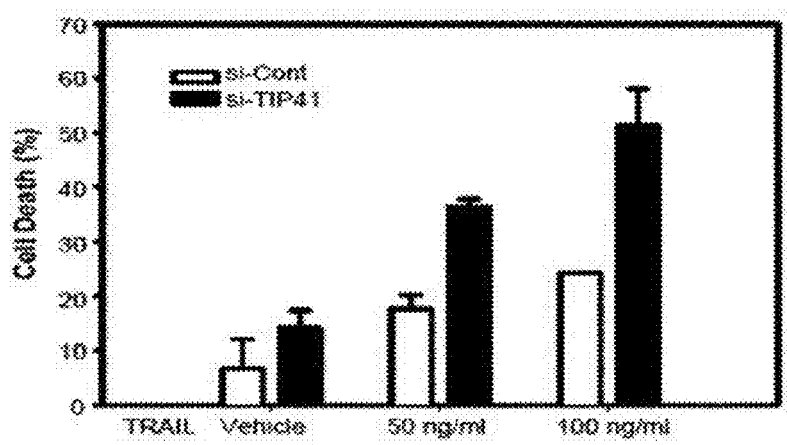

Fig. 8b
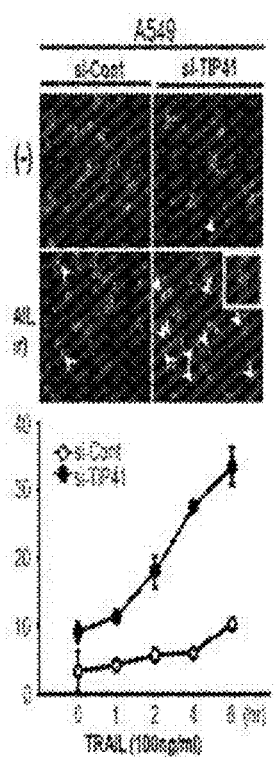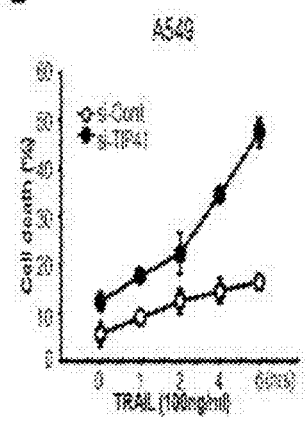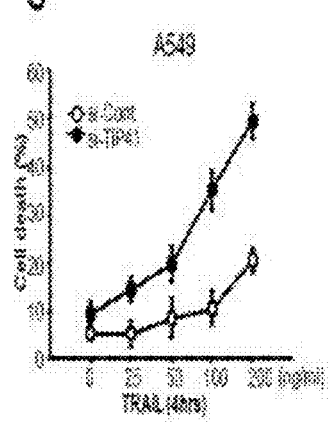

Fig. 8C
A
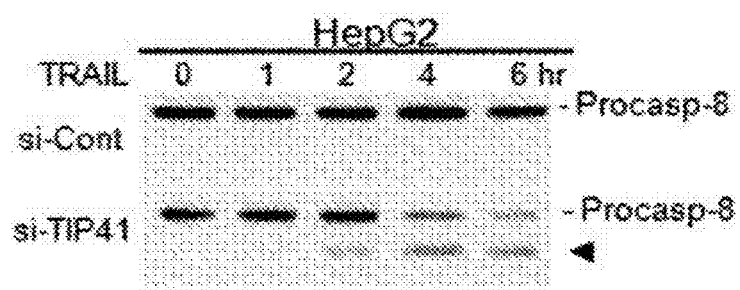
B
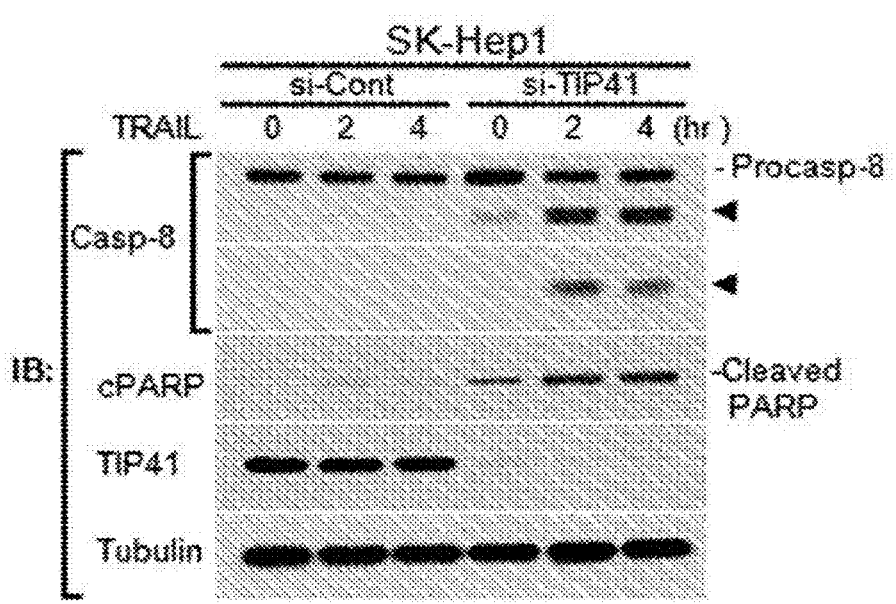

Fig. 10
A. Interaction between TIP41 and PP2Ac
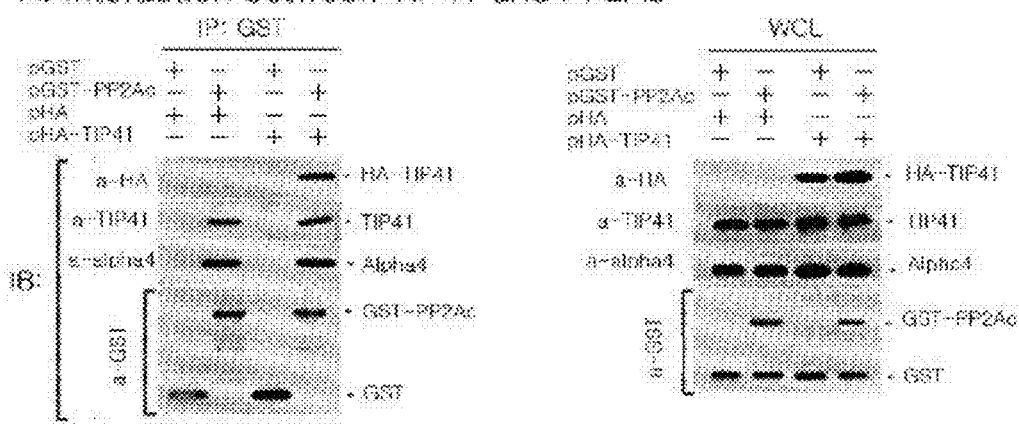
B. Interaction between Tip41 and PP2Ac complex or between Tip41 and MKK7
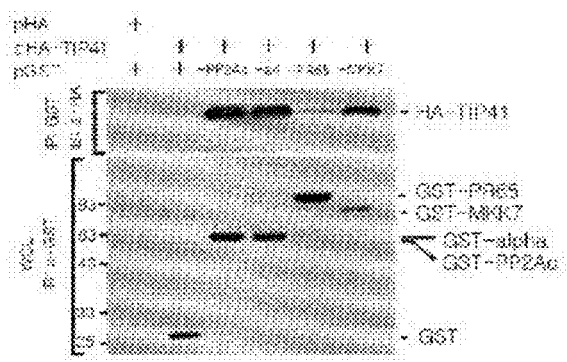

Fig. 11
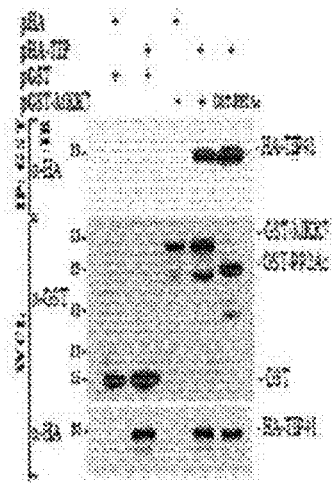
A. Identification of interaction between TIP41 and MKK7 after over-expression of MKK7
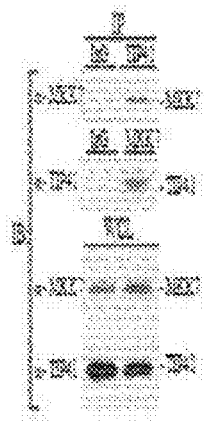
B. Identification of interaction using TIP41 and MKK7 antibody
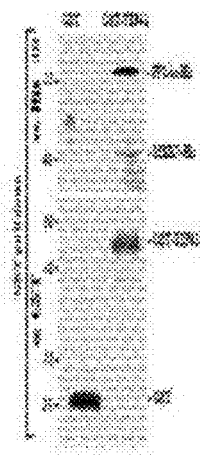
C. Identification of interaction of PP2Ac, TIP41 and MKK7 through In-vitro GST-Pull down Fig. 12
A. TIP41 fragment production
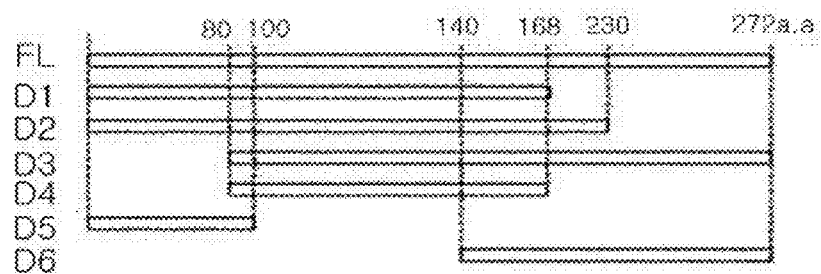
B. Identification of TIP41 binding site that interacts with MKK7
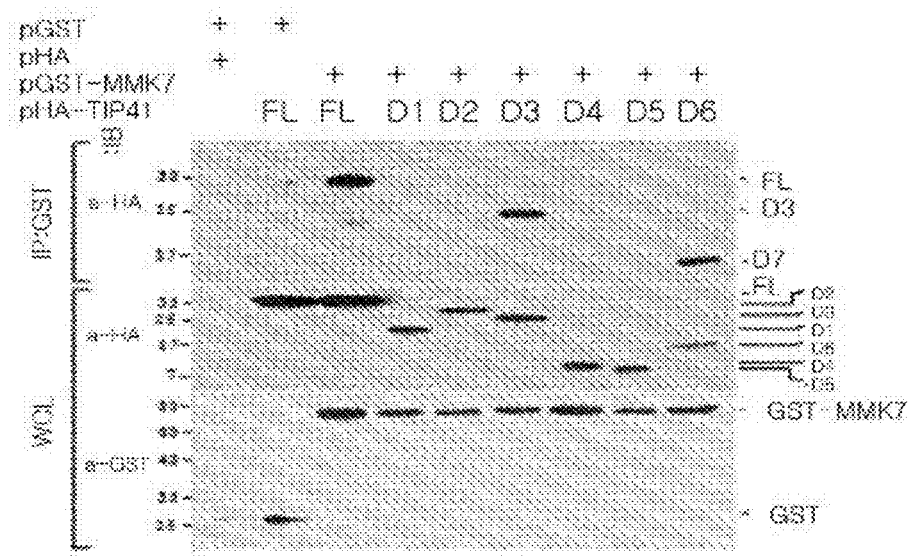

Fig. 13
A. MKK7 fragment production
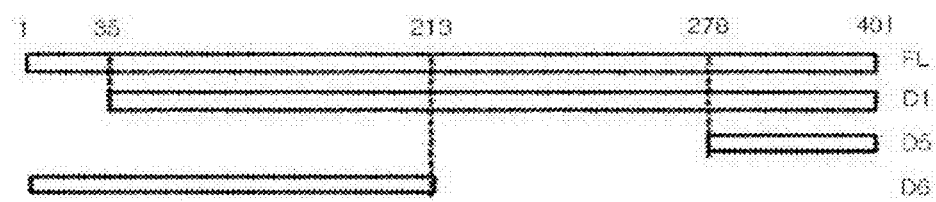
B. Identification of MKK7 binding site that interacts with TIP41
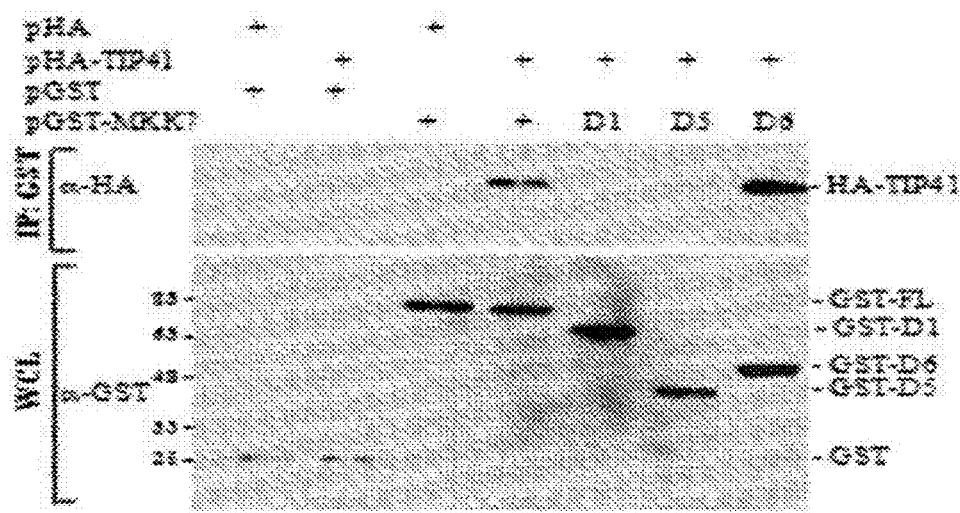

Fig. 14
A. Reduction of apoptosis by repression of MKK7 that interacts with TIP41
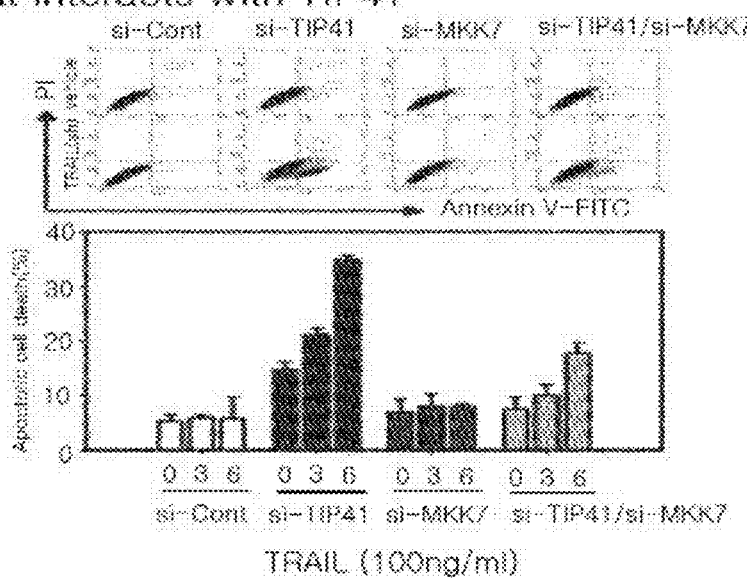
B. Activation of MKK7/JNK pathway by TIP41 repression- in vitro immuno-co-kinase assay
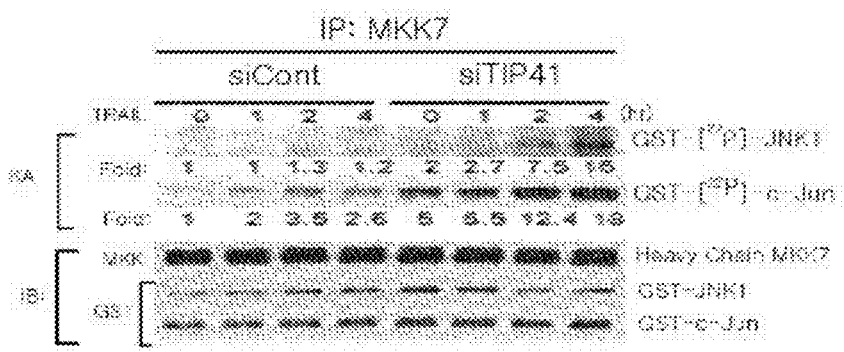

SEQUENCE LISTING

```
<160> NUMBER OF SEQ ID NOS: 36

<210> SEQ ID NO 1
<211> LENGTH: 272
<212> TYPE: PRT
<213> ORGANISM: Homo sapiens

<400> SEQUENCE: 1

Met Met Ile His Gly Phe Gln Ser Ser His Arg Asp Phe Cys Phe Gly
1               5                   10                  15

Pro Trp Lys Leu Thr Ala Ser Lys Thr His Ile Met Lys Ser Ala Asp
            20                  25                  30

Val Glu Lys Leu Ala Asp Glu Leu His Met Pro Ser Leu Pro Glu Met
        35                  40                  45

Met Phe Gly Asp Asn Val Leu Arg Ile Gln His Gly Ser Gly Phe Gly
    50                  55                  60

Ile Glu Phe Asn Ala Thr Asp Ala Leu Arg Cys Val Asn Asn Tyr Gln
65                  70                  75                  80

Gly Met Leu Lys Val Ala Cys Ala Glu Glu Trp Gln Glu Ser Arg Thr
                85                  90                  95

Glu Gly Glu His Ser Lys Glu Val Ile Lys Pro Tyr Asp Trp Thr Tyr
            100                 105                 110

Thr Thr Asp Tyr Lys Gly Thr Leu Leu Gly Glu Ser Leu Lys Leu Lys
            115                 120                 125
```

```
Val Val Pro Thr Thr Asp His Ile Asp Thr Glu Lys Leu Lys Ala Arg
        130                 135                 140

Glu Gln Ile Lys Phe Phe Glu Glu Val Leu Leu Phe Glu Asp Glu Leu
145                 150                 155                 160

His Asp His Gly Val Ser Ser Leu Ser Val Lys Ile Arg Val Met Pro
                165                 170                 175

Ser Ser Phe Phe Leu Leu Leu Arg Phe Phe Leu Arg Ile Asp Gly Val
            180                 185                 190

Leu Ile Arg Met Asn Asp Thr Arg Leu Tyr His Glu Ala Asp Lys Thr
        195                 200                 205

Tyr Met Leu Arg Glu Tyr Thr Ser Arg Glu Ser Lys Ile Ser Ser Leu
    210                 215                 220

Met His Val Pro Pro Ser Leu Phe Thr Glu Pro Asn Glu Ile Ser Gln
225                 230                 235                 240

Tyr Leu Pro Ile Lys Glu Ala Val Cys Glu Lys Leu Ile Phe Pro Glu
                245                 250                 255

Arg Ile Asp Pro Asn Pro Ala Asp Ser Gln Lys Ser Thr Gln Val Glu
            260                 265                 270
```

<210> SEQ ID NO 2
<211> LENGTH: 21
<212> TYPE: DNA
<213> ORGANISM: Artificial Sequence
<220> FEATURE:
<223> OTHER INFORMATION: TIP41 siRNA

<400> SEQUENCE: 2
cctaatgaaa tatcccagta t                                      21

<210> SEQ ID NO 3
<211> LENGTH: 20
<212> TYPE: DNA
<213> ORGANISM: Artificial Sequence
<220> FEATURE:
<223> OTHER INFORMATION: TIP41 forward primer

<400> SEQUENCE: 3
attgaaagcc agagaacaga                                        20

<210> SEQ ID NO 4
<211> LENGTH: 20
<212> TYPE: DNA
<213> ORGANISM: Artificial Sequence
<220> FEATURE:
<223> OTHER INFORMATION: TIP41 reward primer

<400> SEQUENCE: 4
tctcgtgtca ttcattctga                                        20

<210> SEQ ID NO 5
<211> LENGTH: 23
<212> TYPE: DNA
<213> ORGANISM: Artificial Sequence
<220> FEATURE:
<223> OTHER INFORMATION: DR4 forward primer

<400> SEQUENCE: 5
ctcagcggaa tcaatcagct gtg                                    23

<210> SEQ ID NO 6
<211> LENGTH: 25
<212> TYPE: DNA
<213> ORGANISM: Artificial Sequence

```
-continued

<220> FEATURE:
<223> OTHER INFORMATION: DR4 reward primer

<400> SEQUENCE: 6
agaggaacac gacaatcagc cttag                                              25

<210> SEQ ID NO 7
<211> LENGTH: 24
<212> TYPE: DNA
<213> ORGANISM: Artificial Sequence
<220> FEATURE:
<223> OTHER INFORMATION: DR5 forward primer

<400> SEQUENCE: 7
atcaagcggc cccctttttt tcac                                               24

<210> SEQ ID NO 8
<211> LENGTH: 24
<212> TYPE: DNA
<213> ORGANISM: Artificial Sequence
<220> FEATURE:
<223> OTHER INFORMATION: DR5 reward primer

<400> SEQUENCE: 8
ctcattgtca cactcctcga cagc                                               24

<210> SEQ ID NO 9
<211> LENGTH: 20
<212> TYPE: DNA
<213> ORGANISM: Artificial Sequence
<220> FEATURE:
<223> OTHER INFORMATION: DcR1 forward primer

<400> SEQUENCE: 9
tccccaagac cctaaagttc                                                    20

<210> SEQ ID NO 10
<211> LENGTH: 20
<212> TYPE: DNA
<213> ORGANISM: Artificial Sequence
<220> FEATURE:
<223> OTHER INFORMATION: DcR1 reward primer

<400> SEQUENCE: 10
ggcaccaaat tcttcaacac                                                    20

<210> SEQ ID NO 11
<211> LENGTH: 20
<212> TYPE: DNA
<213> ORGANISM: Artificial Sequence
<220> FEATURE:
<223> OTHER INFORMATION: DcR2 forward primer

<400> SEQUENCE: 11
gcacagaggg tgtggattac                                                    20

<210> SEQ ID NO 12
<211> LENGTH: 20
<212> TYPE: DNA
<213> ORGANISM: Artificial Sequence
<220> FEATURE:
<223> OTHER INFORMATION: DcR2 reward primer

<400> SEQUENCE: 12
gagcagatgc ctttgaggta                                                    20
```

```
<210> SEQ ID NO 13
<211> LENGTH: 18
<212> TYPE: DNA
<213> ORGANISM: Artificial Sequence
<220> FEATURE:
<223> OTHER INFORMATION: beta-2-microglobulin forward primer

<400> SEQUENCE: 13
ctcgctccgt ggccttag                                                 18

<210> SEQ ID NO 14
<211> LENGTH: 18
<212> TYPE: DNA
<213> ORGANISM: Artificial Sequence
<220> FEATURE:
<223> OTHER INFORMATION: beta-2-microglobulin reward primer

<400> SEQUENCE: 14
caaatgcggc atcttcaa                                                 18

<210> SEQ ID NO 15
<211> LENGTH: 28
<212> TYPE: DNA
<213> ORGANISM: Artificial Sequence
<220> FEATURE:
<223> OTHER INFORMATION: TIP41 forward primer for cloning

<400> SEQUENCE: 15
cgggtaccaa atgatgatcc acggcttc                                      28

<210> SEQ ID NO 16
<211> LENGTH: 27
<212> TYPE: DNA
<213> ORGANISM: Artificial Sequence
<220> FEATURE:
<223> OTHER INFORMATION: TIP41 reward primer for cloning

<400> SEQUENCE: 16
cccggatcct tattccactt gtgtact                                       27

<210> SEQ ID NO 17
<211> LENGTH: 26
<212> TYPE: DNA
<213> ORGANISM: Artificial Sequence
<220> FEATURE:
<223> OTHER INFORMATION: PP2Ac forward primer for cloning

<400> SEQUENCE: 17
cgggatccat ggacgagaag gtgttc                                        26

<210> SEQ ID NO 18
<211> LENGTH: 34
<212> TYPE: DNA
<213> ORGANISM: Artificial Sequence
<220> FEATURE:
<223> OTHER INFORMATION: PP2Ac reward primer for cloning

<400> SEQUENCE: 18
atagtttagc ggccgcttac aggaagtagt ctgg                               34

<210> SEQ ID NO 19
<211> LENGTH: 27
<212> TYPE: DNA
<213> ORGANISM: Artificial Sequence
<220> FEATURE:
<223> OTHER INFORMATION: MKK7 forward primer for cloning
```

<400> SEQUENCE: 19
ccgctcgaga tggcggcgtc ctccctg                                           27

<210> SEQ ID NO 20
<211> LENGTH: 26
<212> TYPE: DNA
<213> ORGANISM: Artificial Sequence
<220> FEATURE:
<223> OTHER INFORMATION: MKK7 reward primer for cloning

<400> SEQUENCE: 20
ggggtacccc tgaagaaggg caggtg                                            26

<210> SEQ ID NO 21
<211> LENGTH: 26
<212> TYPE: DNA
<213> ORGANISM: Artificial Sequence
<220> FEATURE:
<223> OTHER INFORMATION: alpha4 forward primer for cloning

<400> SEQUENCE: 21
cgggatccat ggctgctgag gacgag                                            26

<210> SEQ ID NO 22
<211> LENGTH: 34
<212> TYPE: DNA
<213> ORGANISM: Artificial Sequence
<220> FEATURE:
<223> OTHER INFORMATION: alpha4 reward primer for cloning

<400> SEQUENCE: 22
atagtttagc ggccgctcag cccatgttct gtcg                                   34

<210> SEQ ID NO 23
<211> LENGTH: 26
<212> TYPE: DNA
<213> ORGANISM: Artificial Sequence
<220> FEATURE:
<223> OTHER INFORMATION: PR65 forward primer

<400> SEQUENCE: 23
cgggatccat ggcggcggcc gacggc                                            26

<210> SEQ ID NO 24
<211> LENGTH: 34
<212> TYPE: DNA
<213> ORGANISM: Artificial Sequence
<220> FEATURE:
<223> OTHER INFORMATION: PR65 reward primer

<400> SEQUENCE: 24
atagtttagc ggccgctcag gcgagagaca gaac                                   34

<210> SEQ ID NO 25
<211> LENGTH: 26
<212> TYPE: DNA
<213> ORGANISM: Artificial Sequence
<220> FEATURE:
<223> OTHER INFORMATION: TIP41-DI reward primer for cloning

<400> SEQUENCE: 25
cgggatccca ggcttgaaac tccatg                                            26

```
<210> SEQ ID NO 26
<211> LENGTH: 27
<212> TYPE: DNA
<213> ORGANISM: Artificial Sequence
<220> FEATURE:
<223> OTHER INFORMATION: TIP41-D2 reward primer for cloning

<400> SEQUENCE: 26
cgggatccgg aagtggaac atgcatc                                        27

<210> SEQ ID NO 27
<211> LENGTH: 27
<212> TYPE: DNA
<213> ORGANISM: Artificial Sequence
<220> FEATURE:
<223> OTHER INFORMATION: TIP41-D3 forward primer for cloning

<400> SEQUENCE: 27
ggggtaccat gcttaaagtg gcctgtg                                       27

<210> SEQ ID NO 28
<211> LENGTH: 26
<212> TYPE: DNA
<213> ORGANISM: Artificial Sequence
<220> FEATURE:
<223> OTHER INFORMATION: TIP41-D4 forward primer for cloning

<400> SEQUENCE: 28
cgggatccat gcttaaagtg gcctgt                                        26

<210> SEQ ID NO 29
<211> LENGTH: 27
<212> TYPE: DNA
<213> ORGANISM: Artificial Sequence
<220> FEATURE:
<223> OTHER INFORMATION: TIP41-D4 reward primer for cloning

<400> SEQUENCE: 29
ccgctcgagc aggcttgaaa ctccatg                                       27

<210> SEQ ID NO 30
<211> LENGTH: 26
<212> TYPE: DNA
<213> ORGANISM: Artificial Sequence
<220> FEATURE:
<223> OTHER INFORMATION: TIP41-D5 reward primer for cloning

<400> SEQUENCE: 30
cgggatccgt gttcaccctc cgtcct                                        26

<210> SEQ ID NO 31
<211> LENGTH: 27
<212> TYPE: DNA
<213> ORGANISM: Artificial Sequence
<220> FEATURE:
<223> OTHER INFORMATION: TIP41-D6 forward primer for cloning

<400> SEQUENCE: 31
cgggatccaa attgaaagcc agagaac                                       27

<210> SEQ ID NO 32
<211> LENGTH: 26
<212> TYPE: DNA
<213> ORGANISM: Artificial Sequence
<220> FEATURE:
<223> OTHER INFORMATION: MKK7-D1 forward primer for cloning
```

```
<400> SEQUENCE: 32
cgggatcccg cagcatggag agcatt                                          26

<210> SEQ ID NO 33
<211> LENGTH: 26
<212> TYPE: DNA
<213> ORGANISM: Artificial Sequence
<220> FEATURE:
<223> OTHER INFORMATION: MKK7-D5 forward primer for cloning

<400> SEQUENCE: 33
cgggatccgc cggctgtgcc gcctac                                          26

<210> SEQ ID NO 34
<211> LENGTH: 36
<212> TYPE: DNA
<213> ORGANISM: Artificial Sequence
<220> FEATURE:
<223> OTHER INFORMATION: MKK7-D6 reward primer for cloning

<400> SEQUENCE: 34
atagtttagc ggccgctaaa tgcgctcggg gatggg                               36

<210> SEQ ID NO 35
<211> LENGTH: 419
<212> TYPE: PRT
<213> ORGANISM: Homo sapiens

<400> SEQUENCE: 35
```

Met Ala Ala Ser Ser Leu Glu Gln Lys Leu Ser Arg Leu Glu Ala Lys
1               5                   10                  15

Leu Lys Gln Glu Asn Arg Glu Ala Arg Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Ser Pro Gln His
    50                  55                  60

Pro Thr Pro Pro Ala Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
        115                 120                 125

Gly Thr Cys Gly Gln Val Trp Lys Met Arg Phe Arg Lys Thr Gly His
    130                 135                 140

Val Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

```
                -continued

His Arg Asp Val Lys Pro Ser Asn Ile Leu Leu Asp Glu Arg Gly Gln
            245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
            275                 280                 285

Ile Asp Pro Pro Asp Pro Thr Lys Pro Asp Tyr Asp Ile Arg Ala Asp
            290                 295                 300

Val Trp Ser Leu Gly Ile Ser Leu Val Glu Leu Ala Thr Gly Gln Phe
305                     310                 315                 320

Pro Tyr Lys Asn Cys Lys Thr Asp Phe Glu Val Leu Thr Lys Val Leu
            325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
            355                 360                 365

Pro Lys Tyr Asn Lys Leu Leu Glu His Ser Phe Ile Lys Arg Tyr Glu
            370                 375                 380

Thr Leu Glu Val Asp Val Ala Ser Trp Phe Lys Asp Val Met Ala Lys
385                     390                 395                 400

Thr Glu Ser Pro Arg Thr Ser Gly Val Leu Ser Gln Pro His Leu Pro
            405                 410                 415

Phe Phe Arg

<210> SEQ ID NO 36
<211> LENGTH: 19
<212> TYPE: DNA
<213> ORGANISM: Artificial Sequence
<220> FEATURE:
<223> OTHER INFORMATION: MKK7 siRNA

<400> SEQUENCE: 36
taagctactt gaacacagc                                              19
```

COMPOSITION FOR ENHANCING TRAIL SENSITIVITY COMPRISING INHIBITORS FOR EXPRESSION OR ACTIVITY OF TIP41 AS A TARGET GENE OF TRAIL SENSITIZER

CROSS-REFERENCES TO RELATED APPLICATION

This patent application is a U.S. national phase under 35 U.S.C 371 of PCT/KR2011/002300 filed on Apr. 1, 2011, which claims the benefit of priority from Korean Patent Applications No. 10-2010-0030004, filed on Apr. 1, 2010, the contents of which are incorporated herein by reference in its entirety.

BACKGROUND OF THE INVENTION

1. Field of the Invention

The present invention relates to a composition comprising TIP41 expression or activity inhibitor, for increasing TRAIL sensitivity.

2. Description of the Related Art

Cancer is the biggest threatening disease to human society; it is generated due to a cell line mutation, which leads to uncontrollable and infinite divisions and immortality of the cells. Causes of cancers include external or environmental factors, such as chemicals, viruses, bacteria and ionizing radiation, and internal factors, such as congenital gene mutation (Klaunig & Kamendulis, Annu Rev Pharmacol Toxicol., 44:239-267, 2004).

Cancers found in early stages may be cured with surgeries, radiotherapies and chemotherapies; yet, their side-effects are being issued significantly as well, and patients of late-stage cancers and metastasis cancers end up with terminal illness, which cannot be treated with any specific cure. Also, there have been various biochemical mechanisms related to cancers and the cures have been developed as the follow-ups, yet fundamental cure for cancer has not been provided.

TRAIL (TNF Related Apoptosis Inducing Ligand) is a cytokine involved in TNF (Tumor Necrosis Factor) family, and this acts as a ligand inducing apoptosis by activating death receptor pathway. TRAIL has 4 receptors. Among these, DR 4/5 (Death Receptor 4/5) is known to be over-expressed in cancer cell line, while DcR 1/2 (Decoy Receptor 1/2) is reported in normal cell line. Unlike other receptors, decoy receptors do not have the death domain at the end of c-terminal, therefore, the death signal is not transmitted inside of cell. Thus, cancer treatment using TRAIL is considered as a next-generation anticancer agent having no side effects on normal cell.

Many anticancer agents and cancer repressors developed so far have been reported to have side effects, such as critical cytotoxicity on normal cell due to their nonspecific nature, and the resistance acquisition of cancer cell line due to high mutation rate. However, since it was reported that TRAIL induces apoptosis of cancer cells, not of normal cell in 1997, TRAIL has been considered as a new anticancer drug, which is specific for cancer cell line and also for cancer cell exhibiting resistance to other cancer drugs. However, several cancers, including breast, prostate, uterus, lung, liver and brain tumors, show TRAIL resistance, and it is also reported that continuous treatment of TRAIL to cancer cell line leads to the acquisition of resistance of cancer cell against TRAIL, even for those cells, which were sensitive to TRAIL.

TRAIL resistance mechanism is possibly caused due to the inhibitions of intracellular apoptosis signal transduction and DR 4/5s due to over-expression of decoy receptor, DcR 1 and 2, and in particular, the resistance acquisition due to change of intracellular signaling system is considered to be a more plausible explanation. The major cause in change of signal transduction is known to be over-expression of antiapoptotic protein, which inhibits proapoptotic proteins functions. Therefore, the development of TRAIL sensitizer, which increases cancer cell line specific apoptosis by overcoming TRAIL resistance, is an essentially-required research field.

It has been reported that the TRAIL-mediated cell death pathways play an important role in the diseases including rheumatoid arthritis, diabetic renal disease, and degenerative brain disease, as well as cancer (Journal of Korean Colledge of Rheumatology Vol. 12, No. 2, June, 2005; J AM Sco Nephrol 19: 904-914 (2008); Cell Death Differ. 2003 January; 10(1):134-41). A variety of approaches have thus been made to use TRAIL for relief and treatment of symptoms of autoimmune disease including arthritis, by inducing death of over-expressed immunocyte. Accordingly, TRAIL can be efficaciously used not only for treatment of the various cancers mentioned above, but also for treatment of T-cell-mediated autoimmune disease including experimental autoimmune encephalomyelitis (EAE), rheumatoid arthritis, and type I diabetes.

TIP41 gene, also called TIPRL (TOR Signaling Pathway Regulator-Like), was first isolated from yeast. TIP41 protein is known to be a negative regulator of TOR signaling system that reacts to rapamycin by interacting with TAP42 protein (Jacinto E et al, Mol. cell. 8 (5): 1017-26, 2001). Human TIP41 gene has 37% homogenous to yeasts TIP41, and is known to activate the signaling systems of MAPK and NF-kappaB (Matsuda A et al, Oncogene., 22 (21): 3307-3318, 2003). Unlike Tip41 in yeast, human TIP41 is expected to activate proliferation of cell, but the function of human TIP41 gene regarding liver cancer, stomach cancer or occurrence of cancer has never been reported yet.

Hence, the present inventors have completed the development by demonstrating that the apoptosis in TRAIL resistant cancer cell was significantly increased by the treatment of TRAIL and TIP41 depletion using siRNA (small interfering RNA) against TIP41. In addition, the induction of apoptosis was observed not only in liver cancer cell, but also in lung cancer cell and colorectal cancer cell, exhibiting TRAIL resistance. Furthermore, the effect was also confirmed in the size reduction of tumor on mice, which were injected with siRNA against TIP41 and TRAIL.

SUMMARY OF THE INVENTION

The present invention provides a composition including TIP41 protein expression or activity inhibitor, for increasing TRAIL sensitivity.

In order to achieve the object, the present invention provides a composition comprising TIP41 protein expression or activity inhibitor, for increasing TRAIL sensitivity.

The present invention also provides an anti-cancer adjuvant comprising inhibitors for expression or activity of TIP41 protein.

The present invention also provides a composition for prevention and treatment of cancer comprising the anti-cancer adjuvant according to the present invention.

The present invention also provides a method of screening a composition for prevention or treatment of cancer. The present invention also provides a method for enhancing sensitivity of cancer to TRAIL, comprising a step of administering a pharmaceutically effective amount of TIP41 protein expression or activity inhibitor into a subject with TRAIL-mediated apoptosis-related disease.

The present invention also provides a method for prevention of cancer, comprising a step of administering a pharmaceutically effective amount of TIP41 protein expression or activity inhibitor into a subject.

The present invention also provides a method for treatment of cancer, comprising a step of administering a pharmaceutically effective amount of TIP41 protein expression or activity inhibitor into a subject with cancer.

The present invention also provides a TIP41 protein expression or activity inhibitor for use in increasing TRAIL sensitivity during treatment of TRAIL-mediated apoptosis-related disease.

Furthermore, the present invention provides a TIP41 protein expression or activity inhibitor for use as anticancer adjuvant.

When the liver cancer cell lines showing resistance to TRAIL are treated with TIP41 siRNA to inhibit expression of TIP41 and then, treated with TRAIL, specific apoptosis of cancer cell lines is induced. The same effect is found in cases of not only liver cancer but also lung cancer and colon cancer having resistance against TRAIL. In addition, the depletion of TIP41 expression and treatment of TRAIL reduced the tumor size of nude mice, injected with tumor cell. Taken together, the composition of the present invention including TIP41 expression or activity inhibitors may be used for increasing TRAIL sensitivity or as an anti-cancer adjuvant.

BRIEF DESCRIPTION OF THE DRAWINGS

The application of the preferred embodiments of the present invention is best understood with reference to the accompanying drawings, wherein:

FIG. 1 is a diagram showing increased expression of TIP41 in liver cancer tissue, and confirming the inhibition of TIP41 upon transfecting TIP41 siRNA into Huh7 liver cancer cell lines, and then treating with TRAIL:

FIG. 1A is a diagram showing increased expression of TIP41 in liver cancer tissue;

FIG. 1B is a diagram showing increased level of TIP41 in liver cancer tissue, regardless of HBV infection, compared with that of TIP41 in the surrounding normal tissue using western blot analysis FIG. 1C is a diagram showing the inhibition of TIP41 expression by transfecting TIP41 siRNA into Huh7 liver cancer lines, and then treating with TRAIL;

Figure 9A:
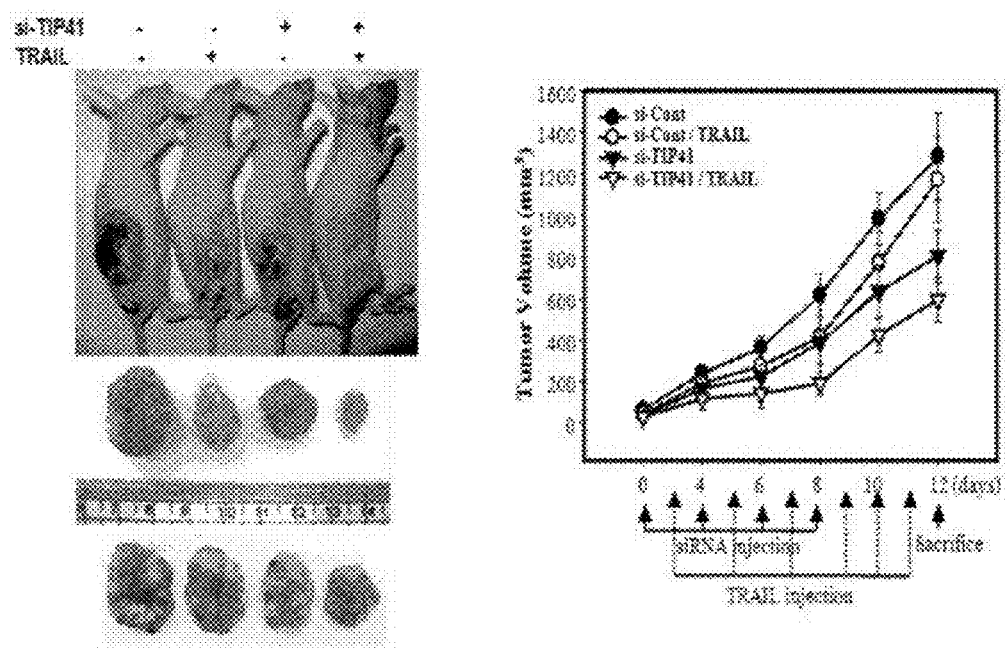

si-cont: control group siRNA; and
si-TIP41: TIP41 siRNA.

FIG. 2 is a diagram confirming the induced apoptosis of cancer cells upon transfecting TIP41 siRNA into Huh7 liver cancer cell, and then treating with TRAIL:

FIG. 2A is a diagram showing apoptosis of cancer cells through nuclear chromatin staining method upon transfecting TIP41 siRNA into Huh7 liver cancer cell, and then treating with TRAIL on a time-dependent manner;

si-cont: control group siRNA;
si-1017: TIP41 siRNA;

FIG. 2B is a diagram analyzing with FACS using Annexin V-FITc/PI staining method upon transfecting TIP41 siRNA into Huh7 liver cancer cell, and then treating with TRAIL on a time-dependent manner;

si-cont: control group siRNA;
si-TIP41: TIP41 siRNA

FIG. 2C is a diagram analyzing with FACS using Annexin V-FITc/PI staining method upon transfecting TIP41 siRNA into Huh7 liver cancer cells, and then treating with TRAIL on a concentration-dependent manner;

si-cont: control group siRNA; and
si-TIP41: TIP41 siRNA.

FIG. 3 is a diagram confirming the activation of pro-apoptotic proteins in apoptosis of cancer cells upon transfecting TIP41 siRNA into Huh7 liver cancer cell, and then treating with TRAIL on a time-dependent manner:

FIG. 3A is a diagram confirming the activation of caspase-3, -8, -9 and PARP upon transfecting TIP41 siRNA into Huh7 liver cancer lines, and then treating with TRAIL on a time-dependent manner;

si-cont: control group siRNA;
si-TIP41: TIP41 siRNA;

FIG. 3B is a diagram confirming the release of cytochrome C to cytosol upon transfecting TIP41 siRNA into Huh7 liver cancer lines, and then treating with TRAIL on a time-dependent manner;

si-cont: control group siRNA; and
si-TIP41: TIP41 siRNA.

FIG. 4 is a diagram showing the involvement of JNK pathway in apoptosis of Huh7 liver cancer cell which was subjected to TIP41 siRNA and TRAIL treatment:

FIG. 4A is a diagram showing the activation of JNK pathway upon transfecting TIP41 siRNA into Huh7 liver cancer cell, and then treating with TRAIL on a time-dependent manner;

si-cont: control group siRNA;
si-TIP41: TIP41 siRNA;

FIG. 4B is a diagram showing the treatment of JNK inhibitor reduced apoptosis of Huh7 liver cancer cell, which was subjected to TIP41 depletion and TRAIL treatment;

si-cont: control group siRNA;
si-TIP41: TIP41 siRNA;
Vehicle: 0.3% of dimethyl sulfoxide (DMSO); and
SP600125: JNK inhibitor.

FIG. 5 is a diagram demonstrating that the apoptosis induced from Huh7 liver cancer cell treated with TIP41 siRNA and TRAIL is independent from p53 signaling pathway:

FIG. 5A is a diagram showing that the apoptosis of Huh7 liver cancer cell, which was subjected to TIP41 siRNA and TRAIL treatment, is independently induced from p53 pathway;

si-cont: control group siRNA;
si-TIP41: TIP41 siRNA; and

FIG. 5B is a diagram demonstrating the apoptosis by TIP41 depletion and TRAIL treatment is induced regardless of p53 presence.

FIG. 6 is a diagram showing no relationship between TIP41 depletion and TRAIL receptors:

FIG. 6A is a diagram showing expression levels of TRAIL receptors in various cell lines;

FIG. 6B is a diagram showing expression levels of TRAIL receptors in the Huh7 liver cancer cell lines, which is subjected to TIP41 depletion and TRAIL;

si-cont: control group siRNA;
si-TIP41: TIP41 siRNA; and

FIG. 6C is a diagram showing expression levels of TRAIL receptors depending on the stages of liver cancer tissue.

FIG. 7 is a diagram showing

TIP41 depletion and TRAIL treatment was not able to induce a significant cell death in normal HAEC cells:

FIG. 7A is a diagram showing no significant induction of apoptosis was observed in HAEC cells, which were subjected to TIP41 depletion and TRAIL treatment on a time-dependent manner;

si-cont: control group siRNA;
si-TIP41: TIP41 siRNA;

FIG. 7B is a diagram showing no cleavages of proapoptotic protein involved in apoptosis of HAEC, which was subjected to TIP41 depletion and TRAIL treatment, on a time-dependent manner;
si-cont: control group siRNA; and
si-TIP41: TIP41 siRNA.

FIG. 8 is a diagram showing increased apoptosis in lung, colorectal and liver cancer cell lines, which were subjected with TIP41 depletion and TRAIL treatment.

FIG. 8A is a diagram showing increased apoptosis induced upon transfecting TIP41 siRNA on the A549 lung cancer cell, and then treating with TRAIL on a time-dependent manner, compared to the control group siRNA;
si-cont: control group siRNA;
si-TIP41: TIP41 siRNA;

FIG. 8B is a diagram showing increased apoptosis induced upon transfecting TIP41 siRNA on the A549 lung cancer cell, and then treating with TRAIL on a concentration- or time dependent manner, compared to the control group siRNA;
si-cont: control group siRNA; and
si-TIP41: TIP41 siRNA.

Figure 9B:
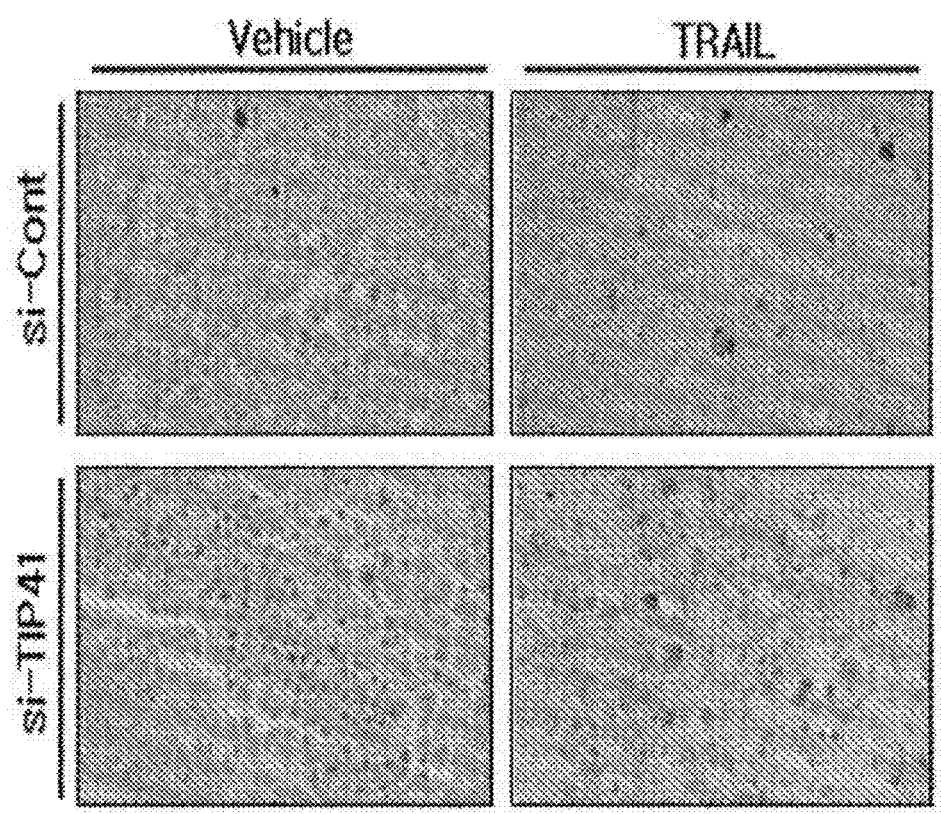
Figure 9C:
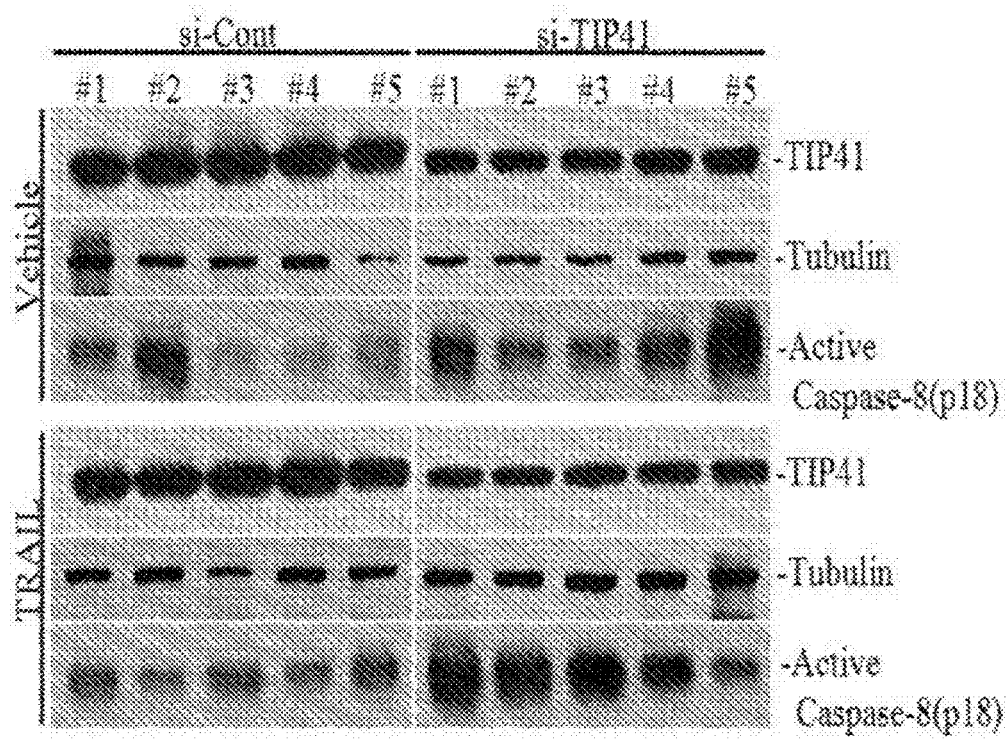

FIG. 8C is a diagram showing increased apoptosis induced upon transfecting TIP41 siRNA on the HepG2, SK-Hep1 liver cancer cells, and then treating with TRAIL on a time-dependent manner, compared to the control group siRNA;
si-cont: control group siRNA;
si-TIP41: TIP41 siRNA;

FIG. 9 is a diagram verifying the anti-apoptotic function of TIP41 through animal experiments:

FIG. 9A is a diagram and graph showing decreased tumor size of the nude mouse transplanted with cancer cells and then injected with TIP41 siRNA and TRAIL;
si-cont: control group siRNA;
si-TIP41: TIP41 siRNA;

FIG. 9B is a diagram showing apoptosis of cells by staining the tumor of nude mice;
si-cont: control group siRNA;
si-TIP41: TIP41 siRNA; and FIG. 9C is a diagram showing the activation of caspase-8 protein involved in apoptosis using the Western Blotting upon dissolving tumor cells of the nude mouse.

FIG. 10 is a diagram showing interactions between TIP41 and PP2Ac;

FIG. 10A shows the result of Western blotting analysis for the interactions between TIP41 and PP2Ac, after PP2Ac was over-expressed; and FIG. 10B is a diagram confirming interactions between TIP41 and PP2Ac complex, and between TIP41 and MKK7.

FIG. 11 is a diagram confirming interactions between TIP41 and PP2Ac complex, and between TIP41 and MKK7:

FIG. 11A is a diagram confirming interactions between TIP41 and PP2Ac complex, and between TIP41 and MKK7, after MKK7 was over-expressed;

FIG. 11B is a diagram confirming interactions between TIP41 and PP2Ac complex, and between TIP41 and MKK7 using immunoprecipitation procedure; and FIG. 11C is a diagram confirming interactions among TIP41, PP2Ac complex and MKK7 using the in vitro GST immunoprecipitation procedure.

FIG. 12 is a diagram confirming the combining site of TIP41 interacting with MKK7:

FIG. 12A is a diagram showing TIP41 fragments prepared for confirming the binding site of TIP41 interacting with MKK7; and FIG. 12B is a diagram showing the combining site of TIP41 interacting with MKK7 using the Western Blotting.

FIG. 13 is a diagram confirming the combining site of MKK7 interacting with TIP41:

FIG. 13A is a diagram showing MKK7 fragments prepared for confirming the binding site of MKK7 interacting with TIP41; and FIG. 13B is a diagram showing the combining site of MKK7 interacting with TIP41 using the Western Blotting.

FIG. 14 is a diagram confirming an apoptosis pathway by MKK7 interacting with TIP41:

FIG. 14A is a diagram confirming decreased apoptosis upon inhibition of MKK7 expression;

FIG. 14B is a diagram demonstrating activation of MKK7/JNK pathway once expression of TIP41 was suppressed;
si-cont: control group siRNA; and
si-MKK7: MKK7 siRNA.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention is described in detail.

The present invention provides a composition, including TIP41 protein expression or activity inhibitor, for increasing TRAIL sensitivity.

It is preferred that the TIP41 protein has amino acid sequence of SEQ. ID. NO: 1, but not limited thereto.

It is preferred that the TIP41 protein expression or activity inhibitor is a TRAIL sensitizer, but not limited thereto.

It is preferred that the TIP41 expression inhibitor is one selected from a group consisting of anti-sense nucleotide, small interfering RNA (siRNA) against TIP41, short hairpin RNA, and complementarily binding to mRNA of TIP41 gene, but not limited thereto.

It is preferred that the inhibitor for activation of TIP41 is one selected from a group consisting of compound, peptide, peptide mimetics, aptamer, antibody, and natural substance, and specifically binding to TIP41, but not limited thereto.

The composition is preferably used for treatment of cancer, inflammatory disease or autoimmune disease using TRAIL.

The cancer is preferably one selected from a group consisting of liver cancer, colon cancer, cervical cancer, kidney cancer, stomach cancer, prostate cancer, breast cancer, brain tumor, lung cancer, uterine cancer, bladder cancer, blood cancer, pancreatic cancer, and any cancer resistant to TRAIL, but not limited thereto.

Further, the inflammatory disease is preferably one selected from a group consisting of dermatis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, Rheumatic fever, systemic lupus erythematosus, fibromyalgia, psoriatic arthritis, degenerative arthritis, rheumatoid arthritis, shoulder joint arthritis, tendinitis, tendonitis, tenosynovitis, peritendinitis, myositis, hepatitis, cystitis, nephritis, sjogren's syndrome, multiple sclerosis, and acute and chronic inflammation, but not limited thereto.

Further, the autoimmune disease is preferably one selected from a group consisting of rheumatoid arthritis, multiple sclerosis, Myasthenia gravis, Graves disease, Hashimoto's throiditis, Addison's disease, vitiligo, systemic sclerosis, Goodpasture syndrome, Becet's disease, Crohn's disease, ankylosing spondylitis, uveitis, thrombocytopenic purpura, Pemphigus vulgaris, diabetes, Autoimmune Anemia, cryoglobulinemia, adrenoleukodystrophy (ALD), and systemic lupus erythematosus, SLE), but not limited thereto.

Antisense Nucleotide

As defined by Watson-Crick base pair, antisense nucleotide binds (hybridizes) to complementary base pairs of DNA, premature-mRNA or mature-mRNA and restricts the flow of genetic information from DNA to protein. The features of antisense nucleotides that are specific to target sequence exceptionally enable them to be multifunctional. Since antisense nucleotides are long chains of monomer units, these can be easily synthesized for target RNA sequences. The recent researches have proven that antisense nucleotide is useful as a biochemical tool for researching target proteins (Rothenberg et al., J. Natl. Cancer Inst., 81:1539-1544, 1999). There has been significant advancement in fields including oligonucleotide chemistry and nucleotide synthesis that shows nuclease resistance, improved cell line adhesion and target binding affinity, therefore usage of antisense nucleotide can be considered as a new type of inhibitor.

Peptide Mimetics

The peptide mimetics is peptide or non-peptide suppressing the binding domain of TIP41, leading into activation of TIP41. The major residues of nonhydrolysis-type peptide analogue include β-turn dipeptide core (Nagai et al. Tetrahedron Lett 26:647, 1985), keto-methylene pseudopeptide group (Ewenson et al. J Med chem 29:295, 1986; and Ewenson et al. in Peptides: Structure and Function (Proceedings of the 9th AmeriCan Peptide Symposium) Pierce chemiCal co. Rockland, Ill., 1985), Azepine (Huffman et al. in Peptides: chemistry and Biology, G. R. Marshall ed., EScOM Publisher: Leiden, Netherlands, 1988), Benzodiazepine (Freidinger et al. in Peptides; chemistry and Biology, G. R. Marshall ed., EScOM Publisher: Leiden, Netherlands, 1988), β-amino alcohol (Gordon et al. Biochem Biophys Res commun 126:419 1985) and substituted γ-lactam ring (Garvey et al. in Peptides: chemistry and Biology, G. R. Marshell ed., EScOM Publisher: Leiden, Netherlands, 1988).

siRNA Molecule

Sense-RNA and antisense-RNA form double strand RNA molecules, and it is preferable that the sense-RNA is a siRNA that partly includes the nucleic acid sequence that is identical to target sequence of continuous nucleotide among part of TIP41 mRNA. It is preferred that siRNA against TIP41 is designed with sense sequence comprising of 10-30 base pairs and anti-sense sequence that complementarily binds to the sense-sequence, but it is not limited thereto, and any double strand RNA molecule that has complementarily binding sense-sequence that targets a base pair of TIP41 genes may be used. It is most preferred that the antisense-sequence has complement sequence with sense-sequence.

Antibody

For TIP41 antibody, either of antibody prepared by injection of TIP41 or commercially available one may be used. Also, the antibody includes multiclonal antibody, monoclonal antibody and fragments that can bind to epitopes.

Multiclonal antibody may be produced by the conventional method of injecting the TIP41 into an animal, and collecting serum that includes the antibody from the animal by drawing the blood. The multiclonal antibody may be purified with any known method in the field, and may be produced from random animal host, such as goats, rabbits, sheep, monkeys, horses, pigs, cows or dogs.

Monoclonal antibody may be produced with any technology as long as it provides production of antibody molecules through continuous cell line culture. Although it is not limited thereto, the technique may include hybridoma, human B-cell hybridoma and EBV hybridoma. (Kohler G et al., Nature 256:495-497, 1975; Kozbor D et al., J Immunol Methods 81:31-42, 1985; cote R J et al., Proc Natl ACad Sci 80:2026-2030, 1983; and cole S P et al., Mol cell Biol 62:109-120, 1984).

Antibody fragment that includes specific binding site to the TIP41 may be produced. For example, although not limited thereto, F(ab')2 fragment may be produced by degrading antibody molecule with pepsine, and Fab fragment may be produced by reducing F(ab')2 fragment's disulfide bridge. As another method, a monoclonal Fab fragment with desired specificity may be isolated quickly and easily by reducing the size of Fab expression library (Huse W D et al., Science 254: 1275-1281, 1989).

The antibody may be bound to solid substrate, in order to simplify the following procedures such as washing or separation of complex. Examples of solid substrate include synthetic resins, nitrocellulose, glass substrate, metal substrate, glass fiber, microsphere and microbead. Also, the synthetic resins include polyester, polyvinyl chloride, polystyrene, polypropylene, PVDF and nylon.

Aptamer

Aptamer is a single strand nucleic acid (DNA, RNA or modified nucleic acid) that may bind to target molecules with high affinity and specificity, with a stable 3-dimensional structure itself. Since the development of the first aptamer discovery technique, SELEX (Systematic Evolution of Ligands by Exponential Enrichment) (Ellington, A D and Szostak, J W., Nature 346:818-822, 1990), many aptamers that may bind to various target molecules, such as low molecular weight organic matter, peptide and membrane proteins, were found. Since aptamer has unique high affinity (pM level in general) and specificity to target molecules, this is comparable with monoclonal antibodies, and in particular, its potential to be used as an alternative antibody is so high that the aptamer is often called "Chemical Antibody".

In an experimental example of the present invention, overexpression of TIP41 protein liver cancer tissue has been identified with immunohistochemistry and Western blotting. Also, TIP41 protein depletion was identified in liver cancer cell line transfected with TIP41 siRNA (see FIG. 1).

In an experimental example of the present invention, when Huh7 liver cancer cell was treated with TIP41 siRNA and then TRAIL was treated over various time, it was identified that apoptosis was confirmed by nuclear chromatin staining and FACS analysis method. Also, after transfection of TIP41 siRNA to Huh7 liver cancer cell line, and induction of apoptosis through TRAIL on a concentration-dependent manner, the result of FACS analysis identified that apoptosis was further increased in the case of co-treatment with TIP41 siRNA and TRAIL, compared to TRAIL treatment only (see FIG. 2).

In an experimental example of the present invention, after TIP41 siRNA transfection, TRAIL was treated in a time-dependent manner in Huh7 liver cancer cell line, activation of proteins related to apoptosis was observed, particular in Caspase-3, -8, -9 and Poly ADP ribose polymerase (PARP) was identified. Also, the cytochrome C expression in cytosol was identified, which indicated the fact that apoptosis by TRAIL and depletion of TIP41 protein in Huh7 liver cancer cell line occur through a combined form of extrinsic and intrinsic pathways (see FIG. 3).

In an experimental example of the present invention, after time-dependent treatment of TRAIL after TIP41 siRNA transfection in Huh7 liver cancer cell line, the activation of c-Jun N-terminal kinase (JNK) transduction pathway was identified, aiet since reduction of apoptosis by TRAIL and depletion of TIP41 protein was identified in the case of treatment of JNK inhibitor, it was identified from these findings that JNK transduction pathway plays an important role in TRAIL-mediated apoptosis through depletion of TIP41 (see FIG. 4).

In an experimental example of the present invention, to verify the fact that TRAIL-induced apoptosis through TIP41 protein depletion does not induce apoptosis in normal cell line, and take place in a cancer cell line specifically, the effect of p53 protein in TIP41 siRNA and TRAIL-induced apoptosis pathway was studied, and phosphorylation of at ser 15 and 392 was observed. However, when TRAIL was treated to induce apoptosis after TIP41 depletion in p53-deficient HCT116 isogenic HCC cell line, apoptotic cell death was identified. This suggests that TIP41 depletion with TRAIL treatment induces apoptosis regardless of p53 presence (see FIG. 5).

In an experimental example of the present invention, as a result of identification of transcript level of TRAIL receptors in liver and lung cancer cell lines, TRAIL-R2 (DR5) was overexpressed compared to normal cell line. Also, after depletion of TIP41, expression of TRAIL receptors in liver cancer cell line was similarly identified. This suggests that increase of apoptosis through TIP41 depletion does not due to the change in expression of TRAIL receptor (see FIG. 6).

In an experimental example of the present invention, when apoptosis was examined after treating TIP41 siRNA and TRAIL in normal cell line, there was no change in apoptosis in relation to TIP41 siRNA transfection and TRAIL treatment, and no change in activation of proteins that influence apoptosis was confirmed. Therefore, after transfection of siRNA TIP41, it was identified that TRAIL-mediated apoptosis takes place specifically to cancer cell (see FIG. 7).

In an experimental example of the present invention, the induction of apoptosis was identified by TIP41 knockdown using siRNA and treatment of TRAIL to TRAIL-resistant lung and colorectal cancer cell line (see FIG. 8).

In an experimental example of the present invention, in order to verify function of TIP41 through an animal experiment, after transplanting liver cancer cell line to nude mouse, and injecting TIP41 siRNA and TRAIL, reduction of the size of tumor and induction of apoptosis was identified, by activation of proteins related to apoptosis was even greater when TIP41 siRNA and TRAIL were co-injected, rather than when TRAIL alone was injected. (see FIG. 9).

Also, in order to identify apoptosis pathway induced by TIP41 as a TRAIL sensitizer, interaction among MKK7 and components of PP2Ac as a TIP41-binding protein, and PP2 Ac complex was identified (see FIGS. 10 and 11).

More specifically, in order to identify the binding site of MKK7 which binds to TIP41, fragments that include various regions of MKK7 were constructed and the binding site was identified (see FIGS. 12 and 13).

Moreover, in order to identify whether apoptosis pathway induced by depletion of TIP41 and TRAIL treatment results from reduction of interaction between TIP41 and MKK7, apoptosis analysis after the application of knockdown of MKK7 and TIP41 as well as TRAIL treatment in Huh7 liver cancer cell line was performed. In this case, decrease of apoptosis was observed.

The MKK7 knockdown clearly reduced apoptosis induced by TIP41 depletion and TRAIL treatment. Furthermore, we also examined whether JNK activation is involved in TIP41 depletion and TRAIL-induced apoptosis (see FIG. 14).

Therefore, when TIP41 siRNA and TRAIL were treated to TRAIL-resistant liver cancer cell line, apoptosis was induced in TRAIL resistant cancer cells such as liver cancer, lung cancer and colorectal cancer. In addition, when TIP41 siRNA and TRAIL are injected to xenograft mouse produced by human cancer cell line, reduction of tumor size and induction of apoptosis in cancer tissue were observed. Therefore, inhibitor of TIP41 protein expression or TIP41 activation can be used effectively as an active ingredient in a composition for increasing TRAIL sensitivity.

The composition may have one or more active ingredients that exhibit identical or similar function, in addition to TIP41 protein expression or activity inhibitor.

The composition may be administrated orally or parenterally, and in the case of parenteral administration, it may be injected by intraperitoneal injection, intrarectal injection, subcutaneous injection, intravenous injection, intramuscular injection, intrauterine dural injection, intracerebrovascular injection or intrathoracic injection, and may be used as a normal medication type.

The composition may be used alone or in combination with methods including operation, radiation treatment, hormone treatment, chemical treatment and biological reaction regulator.

The daily dosage of the composition is approximately 0.0001 g to 100 mg/kg, preferably 0.001 g to 10 mg/kg, and is preferably administrated once or divided over a few times per day, with the range thereof being variable depending on patients' weight, age, gender, health status, diet, administration time and method, rate of excretion and severity of disease.

The composition of the present invention may be administrated as various non-oral formulations, in case of actual clinical administration; when formulated, it is prepared by using diluents or excipients, such as filler, extender, binder, humectants, disintegrating agent, and surfactant. For parenteral formulations, sterilized solution, hydrophobic solvent, suspending agent, emulsion, lyophilized medication, and suppository are included. For hydrophobic solvent and suspending solvent, vegetable oils such as propylene glycol, polyethylene glycol, and olive oils, and injectable esters, such as ethyl oleate, may be used. For base of suppository, witepsol, macrogol, tween 61, cacao butter, sevum laurinum, and glycerogelatin may be used.

The present invention also provides an anti-cancer adjuvant comprising TIP41 protein expression or activity inhibitor.

It is preferred that the TIP41 protein has amino acid sequence of SEQ. ID. NO: 1, although it is not limited thereto.

It is preferred that the TIP41 protein expression or activity inhibitor is a TRAIL sensitizer, although it is not limited thereto.

It is preferred that the TIP41 protein expression or activity inhibitor is one selected from the group consisting of, for example, but not limited thereto, anti-sense nucleotide, small interfering RNA (siRNA) against TIP41, short hairpin RNA, complementarily binding to mRNA of TIP41 gene, although it is not limited thereto.

It is preferred that the TIP41 activation inhibitor is one selected from the group consisting of compound, peptide, peptide mimetics, aptamer, antibody, and natural substance, specifically binding to TIP41, but not limited thereto.

The cancer is preferably one selected from a group consisting of liver cancer, colon cancer, cervical cancer, kidney cancer, stomach cancer, prostate cancer, breast cancer, brain tumor, lung cancer, uterine cancer, bladder cancer, blood cancer and pancreatic cancer, and any cancer resistant to TRAIL, but not limited thereto.

Further, in the anti-cancer adjuvant, it is preferable that the TIP41 protein expression or activity inhibitor increases the TRAIL sensitivity, but not limited thereto.

In an experimental example of the present invention, TIP41 protein is over-expressed in liver cancer tissue (refer to FIG. 1), and when TIP41 siRNA was transfected to Huh7 liver cancer cell line and TRAIL was treated in various time periods, apoptosis was increased more in comparison to the case with TRAIL treatment only (see FIG. 2). Also, in order to find out apoptosis pathway by TIP41 siRNA and TRAIL when activation of caspase-3, -8, -9 and Poly ADP ribose polymerase as well as JNK transduction pathway related proteins and p53 protein were examined, apoptosis increased more when both TIP41 siRNA and TRAIL were treated, in comparison to the case of TRAIL treatment alone, which exhibits a cancer cell line specific apoptosis is identified to be a cancer cell line specific apoptosis (see FIGS. 3, 4, 5, and 7). Also, when TIP41 protein was repressed, no change in TRAIL receptor was identified (refer to FIG. 6). In addition, by treatment of TIP41 siRNA and TRAIL to cell lines other than liver cancer, those also resistant to TRAIL, apoptotic cell death was identified (see FIG. 8). Moreover, tumor size in xenograft nude mouse was decreased when both TIP41 siRNA and TRAIL were injected, in comparison to the case of separated injections of TRAIL and TIP41 siRNA. Also, activation of protein related to apoptosis and apoptosis in tumor tissue were observed the most effective when both TIP41 siRNA and TRAIL were injected.

Therefore, when TIP41 siRNA and TRAIL are treated to TRAIL-resistant liver cancer cell line, cancer cell line specific apoptosis is induced in TRAIL resistant cancer cells such as liver cancer, lung cancer and colorectal cancer and when TIP41 siRNA and TRAIL are injected to xenograft mouse model, it has an effect to induce apoptosis of cancer cell and decrease in tumor size, therefore it may be used effectively as an anticancer adjuvant that contains inhibitor for expression or activity of TIP41.

The anticancer adjuvant may have one or more active ingredients that show identical or similar function, in addition to inhibitor for expression or activity of TIP41.

The anticancer adjuvant may be administrated orally or parenterally, and in the case of parenteral administration, it may be injected by intraperitoneal injection, intrarectal injection, subcutaneous injection, intravenous injection, intramuscular injection, intrauterine dural injection, intracerebrovascular injection or intrathoracic injection, and may be used as a normal medication type.

The anticancer adjuvant may be used alone or in combination with methods including operation, radiation treatment, hormone treatment, chemical treatment and biological reaction regulator.

The daily dosage of the anticancer adjuvant is approximately 0.0001 g to 100 mg/kg, preferably 0.001 g to 10 mg/kg, and is preferably administrated once or divided over a few times per day, with the range thereof being variable depending on patients' weight, age, gender, health status, diet, administration time and method, rate of excretion and severity of disease.

The anticancer adjuvant of the present invention may be administrated as various parenteral formulations, in the case of actual clinical administration; when formulated, this may be prepared by using diluent or excipient, such as filler, extender, binder, humectants, disintegrating agent, and surfactant. For parenteral formulations, sterilized solution, hydrophobic solvent, suspending agent, emulsion, lyophilized medication, and suppository are included. For hydrophobic solvent and suspending solvent, vegetable oils such as propylene glycol, polyethylene glycol, and olive oils, and injectable esters, such as ethyl oleate, may be used. For base of suppository, witepsol, macrogol, tween 61, cacao butter, sevum laurinum, and glycerogelatin may be used.

The present invention also provides a composition for prevention and treatment of cancer comprising the anti-cancer adjuvant according to the present invention.

In one embodiment, when TIP41 protein expression or activity inhibitor of the present invention is treated in combination with TRAIL, cancer-specific apoptosis rate was increased in a variety of cancer cell lines having resistance to TRAIL, such as liver, lung and colorectal cancer cell lines. Further, in vivo effect of cancer-specific apoptosis of the TIP41 protein expression or activity inhibitor of the present invention was detected in a nude model implanted with cancer cell line.

Therefore, the anti-cancer adjuvant comprising TIP41 protein expression or activity inhibitor can be used as an active ingredient of the composition for the prevention and treatment for cancer.

The composition may have one or more active ingredient that shows identical or similar function, in addition to inhibitor for expression or activity of TIP41.

The composition may be administrated orally or parenterally, and in the case of parenteral administration, the composition may be injected by intraperitoneal injection, intrarectal injection, subcutaneous injection, intravenous injection, intramuscular injection, intrauterine dural injection, intracerebrovascular injection or intrathoracic injection, and may be used as a normal medication type.

The composition may be used alone or in combination with methods including operation, radiation treatment, hormone treatment, chemical treatment and biological reaction regulator.

The daily dosage of the composition is approximately 0.0001 g to 100 mg/kg, preferably 0.001 g to 10 mg/kg, and is preferably administrated once or divided over a few times per day, with the range thereof being variable depending on patients' weight, age, gender, health status, diet, administration time and method, rate of excretion and severity of disease.

The composition of the present invention may be administrated as various parenteral formulations, in the case of actual clinical administration; when formulated, it is prepared by using diluent or excipient, such as filler, extender, binder, humectants, disintegrating agent, and surfactant. For parenteral formulations, sterilized solution, hydrophobic solvent, suspending agent, emulsion, lyophilized medication, and suppository are included. For hydrophobic solvent and suspending solvent, vegetable oils such as propylene glycol, polyethylene glycol, and olive oils, and injectable esters, such as ethyl oleate, may be used. For base of suppository, witepsol, macrogol, tween 61, cacao butter, sevum laurinum, and glycerogelatin may be used.

The present invention also provides a method of screening a composition for prevention or treatment of cancer.

The method of screening a composition for the prevention or treatment of cancer may preferably include:

1) treating a sample substance to cancer cell line as an experimental group;

2) measuring binding level of between TIP41 and PP2Ac or between TIP41 and MKK7 protein in the step 1); and 3) selecting the substance that reduced the binding level of between TIP41 and PP2Ac or between TIP41 and MKK7 protein of the step 2), compared with the control untreated with the sample substance of the step 1), although it is not limited thereto.

It is preferred that the cancer is one selected from the group consisting of liver cancer, colorectal cancer, cervical cancer, kidney cancer, stomach cancer, prostate cancer, breast cancer, brain tumor, lung cancer, uterine cancer, colon cancer, blood cancer and pancreatic cancer, and more preferably, the cancer is liver cancer, lung cancer or colorectal cancer, but it is not limited thereto; and it is preferred that all cancers with resistance to TRAIL are included, but it is not limited thereto.

In the method of screening a composition for the prevention or treatment of cancer of the present invention, it is preferred that binding level of the protein in step 2) is measured with one selected from the group consisting of immunoprecipitation, ELISA, Western Blotting, Glutathione-S-Transferase (GST) pull down analysis, Protein Chip, Fluorescence Resonance Energy Transfer (FRET), Bimolecular Fluorescence Complementation (BiFC) and Yeast two-Hybrid (Y2H), but it is not limited thereto.

The present invention also provides a method of screening a composition for prevention or treatment of cancer.

The method of screening a composition for the prevention or treatment of cancer may preferably include:

1) treating a sample substance to cancer cell line as an experimental group;
2) measuring activity of MKK7 in the step 1); and
3) selecting the substance that increased activity of MKK7 protein of step 2), compared with the control untreated with the sample substance of the step 1), but not limited thereto.

In the method of screening a composition for the prevention or treatment of cancer of the present invention, it is preferred that the expression level of MKK7 protein of step 2) is measured with one selected from the group consisting of RT-PCR, ELISA, immunohistological staining, Western Blotting and FACS, but it is not limited thereto.

It is preferred that the cancer is one selected from the group consisting of liver cancer, colorectal cancer, cervical cancer, kidney cancer, stomach cancer, prostate cancer, breast cancer, brain tumor, lung cancer, uterine cancer, colon cancer, blood cancer and pancreatic cancer, and more preferably, the cancer is liver cancer, lung cancer or colorectal cancer, but it is not limited thereto; and it is preferred that all cancers with resistance to TRAIL are included, but it is not limited thereto.

The present invention also provides a method of screening a composition for prevention or treatment of cancer.

The method of screening a composition for the prevention or treatment of cancer may preferably include:

1) treating a sample substance to cancer cell line as an experimental group;
2) measuring expression level of PP2Ac in the step 1); and
3) selecting the substance that increased reduced expression level of PP2Ac protein of step 2), compared with the control untreated with the sample substance of the step 1), although not limited thereto.

In the method of screening a composition for the prevention or treatment of cancer of the present invention, it is preferred that the expression level of PP2Ac protein of step 2) is measured with one selected from the group consisting of Immunofluorescence, ELISA, Mass spectrometry, and protein chip, but it is not limited thereto.

It is preferred that the cancer is one selected from the group consisting of liver cancer, colorectal cancer, cervical cancer, kidney cancer, stomach cancer, prostate cancer, breast cancer, brain tumor, lung cancer, uterine cancer, colon cancer, blood cancer and pancreatic cancer, and more preferably, the cancer is liver cancer, lung cancer or colorectal cancer, but it is not limited thereto; and it is preferred that all cancers with resistance to TRAIL are included, but it is not limited thereto.

The present invention also provides a method for enhancing sensitivity of cancer to TRAIL, comprising a step of administering a pharmaceutically effective amount of TIP41 protein expression or activity inhibitor into a subject with TRAIL-mediated apoptosis-related disease.

It is preferred that the TIP41 protein expression or activity inhibitor is a TRAIL sensitizer, but it is not limited thereto.

It is preferred that the TIP41 protein expression or activity inhibitor is one selected from a group consisting of anti-sense nucleotide, short interfering RNA(siRNA) and short hairpin RNA, complementarily combining with mRNA of TIP41 gene, but it is not limited thereto, but it is not limited thereto.

It is preferred that the TIP41 protein expression or activity inhibitor is one selected from the group consisting of compound, peptide, peptide mimetics, aptamer, antibody, and natural substance, specifically binding to TIP41, but it is not limited thereto.

The TRAIL-mediated apoptosis-related disease is a cancer, inflammatory disease or autoimmune disease, but it is not limited thereto.

The cancer is preferably one selected from a group consisting of liver cancer, colon cancer, cervical cancer, kidney cancer, stomach cancer, prostate cancer, breast cancer, brain tumor, lung cancer, uterine cancer, bladder cancer, blood cancer, and pancreatic cancer, but not limited thereto.

Further, the inflammatory disease is preferably one selected from a group consisting of dermatis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, Rheumatic fever, systemic lupus erythematosus, fibromyalgia, psoriatic arthritis, degenerative arthritis, rheumatoid arthritis, shoulder joint arthritis, tendinitis, tendonitis, tenosynovitis, peritendinitis, myositis, hepatitis, cystitis, nephritis, sjogren's syndrome, multiple sclerosis, and acute and chronic inflammation, but not limited thereto.

Further, the autoimmune disease is preferably one selected from a group consisting of rheumatoid arthritis, multiple sclerosis, Myasthenia gravis, Graves disease, Hashimoto's throiditis, Addison's disease, vitiligo, systemic sclerosis, Goodpasture syndrome, Becet's disease, Crohn's disease, ankylosing spondylitis, uveitis, thrombocytopenic purpura, Pemphigus vulgaris, Diabetes, Autoimmune Anemia, cryoglobulinemia, adrenoleukodystrophy (ALD), and systemic lupus erythematosus, SLE), but not limited thereto.

In one embodiment, when TIP41 protein expression or activity inhibitor of the present invention is treated in combination with TRAIL, cancer-specific apoptosis rate was increased in a variety of cancer cell lines having resistance to TRAIL, such as liver, lung and colorectal cancer cell lines. Further, in vivo effect of cancer-specific apoptosis of the TIP41 protein expression or activity inhibitor of the present invention was detected in a nude model implanted with tumor.

Therefore, the TIP41 protein expression or activity inhibitor according to the present invention can be effectively used to enhance the TRAIL sensitivity.

The present invention also provides a method for prevention of cancer, comprising a step of administering a pharmaceutically effective amount of TIP41 protein expression or activity inhibitor into a subject.

The present invention also provides a method for treatment of cancer, comprising a step of administering a pharmaceutically effective amount of TIP41 protein expression or activity inhibitor into a subject with cancer.

It is preferred that the subject is vertebrate, preferably mammals, and more preferably an experimental animals including mouse, rabbit, guinea-pig, hamster, dog, cat, and most preferably, anthropoid animals including chimpanzee or gorilla.

The pharmaceutically effective amount of the TIP41 protein expression or activity inhibitor may vary depending on various factors including injection method, targeted part, or patient's condition. Therefore, the administering amount should be decided appropriately, by considering stability and efficiency when used in human body. The pharmaceutically effective amount of injection may also be estimated in animal experiment and adapted for use in human. For information about the factors to be considered in determining the pharmaceutically effective amount of injection, reference may be made to Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The TIP41 protein expression or activity inhibitor according to an embodiment may include a carrier, an excipient, a diluent which are generally used in biological pharmaceutical preparation, or a combination of two or more of the above. The pharmaceutically acceptable carrier is not strictly limited, provided that the carrier is suitable for delivering TIP41 protein expression or activity inhibitor protein in vivo. By way of example, the carrier may include a mixture of compound, saline solution, sterile water, Ringer's solution, buffered saline, dextrose solution, malto dextrine solution, glycerol, ethanol disclosed in Merck Index, 13th ed., Merck & Co. Inc., or a mixture of one or more of the above. As necessary, the carrier may be added with other general additives including antioxidant, buffer solution, or fungistats. Further, diluent, dispersant, surfactant, binder and lubricant may be additionally added to prepare dosage forms including aqueous solution, suspension, or emulsion, pill, capsule, granule or tablet. Furthermore, a known method, or the method disclosed in Remington's Pharmaceutical Science (Mack Publishing Company, Easton Pa., 18th, 1990) may be used to prepare appropriate dosage form according to diseases or ingredients.

The TIP41 protein expression or activity inhibitor of the present invention may additionally include one or more effective ingredients with the same or similar function. The pharmaceutical composition of the present invention includes from 0.0001 to 10 weight % of the protein with respect to the total weight of The pharmaceutical composition, and preferably includes from 0.001 to 1 weight % of the protein.

Depending on purposes, the TIP41 protein expression or activity inhibitor of the present invention may be non-orally injected (such as intravenous, hypodermic, intraperitoneal, or local application) or orally injected. Further, the administering amount may vary depending on weight, age, gender, health condition of patients, diet, injection time, injection method, elimination rate and seriousness of disease. Daily injection amount of The pharmaceutical composition of the present invention ranges between 0.001 µg~10 mg/kg, and preferably between 0.01 µg~10 mg/kg, and it is preferable to divide the injection from one to several times a day.

The present invention also provides a TIP41 protein expression or activity inhibitor for use in increasing TRAIL sensitivity during treatment of TRAIL-mediated apoptosis-related disease.

Furthermore, the present invention provides a TIP41 protein expression or activity inhibitor for use as anticancer adjuvant.

It is preferred that the TIP41 protein has amino acid sequence of SEQ. ID. NO: 1, but not limited thereto.

It is preferred that the inhibitor of expression or activity of TIP41 protein is a TRAIL sensitizer, but not limited thereto.

It is preferred that the inhibitor for expression of TIP41 is one selected from the group consisting of anti-sense nucleotide, small interfering RNA (siRNA) against TIP41, short hairpin RNA, but it is not limited thereto, complementarily binding to mRNA of TIP41 gene, but not limited thereto.

It is preferred that the inhibitor for activation of TIP41 is one selected from the group consisting of compound, peptide, peptide mimetics, aptamer, antibody, and natural substance, specifically binding to TIP41, but not limited thereto.

The TRAIL-mediated apoptosis-related disease is a cancer, inflammatory disease or autoimmune disease, but not limited thereto.

The cancer is preferably one selected from a group consisting of liver cancer, colon cancer, cervical cancer, kidney cancer, stomach cancer, prostate cancer, breast cancer, brain tumor, lung cancer, uterine cancer, bladder cancer, blood cancer, pancreatic cancer, and any cancer resistant to TRAIL, but not limited thereto.

Further, the inflammatory disease is preferably one selected from a group consisting of dermatis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, Rheumatic fever, systemic lupus erythematosus, fibromyalgia, psoriatic arthritis, degenerative arthritis, rheumatoid arthritis, shoulder joint arthritis, tendinitis, tendonitis, tenosynovitis, peritendinitis, myositis, hepatitis, cystitis, nephritis, sjogren's syndrome, multiple sclerosis, and acute and chronic inflammation, but not limited thereto.

Further, the autoimmune disease is preferably one selected from a group consisting of rheumatoid arthritis, multiple sclerosis, Myasthenia gravis, Graves disease, Hashimoto's throiditis, Addison's disease, vitiligo, systemic sclerosis, Goodpasture syndrome, Becet's disease, Crohn's disease, ankylosing spondylitis, uveitis, thrombocytopenic purpura, Pemphigus vulgaris, Diabetes, Autoimmune Anemia, cryoglobulinemia, adrenoleukodystrophy (ALD), and systemic lupus erythematosus, SLE), but not limited thereto.

Hereinafter, the present invention will be described in detail with reference to experimental examples and formulation examples. However, the following experimental examples and formulation examples are provided only for illustrative purpose of the present invention, and the present invention is not limited by the following experimental examples and formulation examples.

EXAMPLE 1

Confirmation of TIP41 Protein Expression in Tissues of Liver Cancer and Lung Cancer <1-1> Confirmation of TIP41 Expression with Immunostaining The tissue of patient with liver cancer (Chungnam University Medical School, Professor Kim, Jin-Man) was fixed with about 10% neutral buffer formalin solution, paraffin was added and was cut in about 5 an thickness. The section was treated with about 10 mM ascorbic acid buffer (pH 6.0) for about 4 minutes, and was placed in about 0.1 M Tris-buffer saline solution (TBS, pH 7.4), with about 3% peroxide (H2O2) included, for about 30 minutes. The section was treated with Protein Block Solution (DAKO) for about 20 minutes in room temperature, and was reacted with anti-TIP41 antibody for 30 minutes. After washing with 0.1 M TEST (0.1 M TBS containing 0.01% Tween 20), the section was reacted for 30 minutes with nVision anti-rabbit polymer (DAKO) The peroxidase-bound antibody was visualized by reacting it with 3,3-diaminobenzidine (DAB) chromogen substrate solution (DAKO). While observing it under microscope, the reaction was terminated by washing it with 0.1 M TBS when staining was appropriately done, and Olympus BX51 microscope (Olympus, Japan) was used for observation, and Olympus DP 70 camera (Olympus, Japan) was used for imaging.

As the result, over-expression of TIP41 in tumour region of liver cancer tissue, compared to normal region, was observed (FIG. 1A). In addition, compared to surrounding normal tissues of patients with liver cancer and lung cancer (provided by a team of professor Kim, Jin-Man, Chungnam National University), TIP41 proteins were overexpressed in cancer tissues of these patients (Table 1 and 2). The correlation analysis between TIP41 expression and cancer stage showed that positive expression of TIP41 was significantly associated with a higher stage of NSCLC, lung cancer (P=0.045), suggesting the correlation of TIP41 expression with NSCLC progression (Table 2). These data indicate that TIP41 expression is highly overexpressed in HCC and NSCLC cells.

TABLE 1

Expression level of TIP41 in clinical tissues of liver cancer (HCC) (IHC method)

| HCC stage | total, n | TIP41 Negative, n(%) | TIP41 Positive, n(%) | P |
|---|---|---|---|---|
| I | 4 | 1(25.0%) | 3(75.0%) | 0.490 |
| II | 19 | 2(10.5%) | 17(89.5%) | |
| IIIA | 6 | 4(66.7%) | 2(33.3%) | |
| IIIC | 32 | 7(21.9%) | 25(78.1%) | |
| IV | 6 | 1(16.7%) | 6(83.3%) | |

P value was calculated from linear by linear associations.

TABLE 2

Expression level of TIP41 in clinical tissues of lung cancer (Non small cell lung cancer, NSCLC) (IHC method)

| NSCLC stage | total, n | TIP4 Negative, n(%) | TIP4 Positive, n(%) | P |
|---|---|---|---|---|
| I | 25 | 10(60.0%) | 15(40.0%) | 0.045 |
| I | 47 | 16(34.0%) | 31(66.0%) | |
| II | 19 | 3(15.8%) | 16(84.2%) | |
| II | 31 | 6(19.4%) | 25(80.6%) | |
| III | 47 | 4(8.5%) | 43(91.5%) | |
| III | 5 | 1(16.7%) | 5(83.3%) | |
| IV | 4 | 0(0%) | 4(100%) | |

P value was calculated from linear by linear associations.

<1-2> Confirmation of TIP41 Expression Using Western Blotting

By using protein extracted from liver cancer tissue and closely located normal tissue from 7 liver cancer patients with Hepatitis B Virus (HBV) and 7 liver cancer patients without HBV (Chungnam University Medical School), the expression level of TIP41 protein was examined with Western Blotting.

Tissue was lysed with lysis buffer [20 mM HEPES (4-(2-hydroxyethyl)-1-piperazineethanesulfonic acid) (pH7.5), 150 mM Nacl, 1 mM EDTA (ethylene diamine tetraacetic acid), 2 mM EGMA (ethylene glycol tetraacetic acid), 1% Triton X-100, 10% glycerol, Protease inhibitor cocktail, phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for an hour, to stop any nonspecific reaction. After about an hour, the nitrocellulose membrane was reacted for over 12 hours in about 4° C. with 1:2,000 TIP41 (Betyl Laboratories, USA) and 1:5,000 GAPDH (Abformtier, Korea), washed with 0.1% TEST (Tris-Buffered Saline Tween-20) for three times, about 10 minutes per washing, and secondary antibody of anti-mouse (Pierce, USA) anti-rabbit (Pierce, USA) were reacted for about an hour in room temperature. Then this was washed for three times with 0.1% TEST, about 10 minutes per washing, and the expression was identified with chemiluminescence reagent. As the quantitative control group of each tissue, GAPDH (Glyceraldehyde-3-phosphate dehydrogenase), a housekeeping gene, was used.

As the result, over-expression of TIP41 in 7 liver cancer patients with Hepatitis B Virus (HBV) and 7 liver cancer patients without HBV was identified (FIG. 1B).

<1-3> Culture of Liver Cancer Cell Line

The human Huh7 liver cancer cell line, distributed from Korean Cell Line Bank, was cultured in Dulbecco's modified eagle's medium (DMEM) with 10% fetal bovine serum and at 37° C. with 5% $CO_2$. Huh7 liver cancer cell line with $1\times10^6$ cells/100 mm dish was cultured for 24 hours and then transfected with siRNA.

<1-4> Transfection of siRNA

In order to examine TIP41's function as TRAIL sensitizer, siRNA sequence effectively represses TIP41 was chosen and synthesis of TIP41 siRNA was performed (Dharmacon RNAi Technologies, USA).

The $2\times10^5$ liver cancer cell line cultured from <1-3> was planted in 60 mm culture dish, and was transfected with siRNA using lipofectamine RNAimax (invitrogen), following the instructions of the manufacturer's instructions. After about 72 hours, the transfected cell were treated with TRAIL (100 ng/ml) for about 0, 0.5, 1, 2, 3, 4, 6 hours; lysis buffer was used in each time period to collect protein from the cell, and Western Blotting was done. After lysing the cell with lysis buffer ([20 mM HEPES (pH7.5), 150 mM NaCl, 1 mM EDTA, 2 mM EGTA, 1% Triton X-100, 10% glycerol, Protease inhibitor cocktail, Phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for about an hour, to stop any nonspecific reaction. After about an hour, the nitrocellulose membrane was reacted for over 12 hours in about 4° C. with 1:2,000 TIP41 (Betyl Laboratories, USA) and 1:5,000 GAPDH (Abformtier, Korea), washed with 0.1% TEST (Tris-Buffered Saline Tween-20) for three times, about 10 minutes per washing, and secondary antibody of anti-mouse (Pierce, USA) anti-rabbit (Pierce, USA) were reacted for about an hour in room temperature. Then this was washed for three times with 0.1% TEST, about 10 minutes per washing, and the expression was identified with chemiluminescence reagent. As the quantitative control group of each tissue, GAPDH (Glyceraldehyde-3-phosphate dehydrogenase), a housekeeping gene, was used.

The TIP41 siRNA sequence used was 5'-CCT AAT GAA ATA TCC CAG TAT-3' (SEQ. ID. NO: 2).

As the result, whether TRAIL treatment was done or not, TIP41 protein was completely repressed after treatment of TIP41 siRNA (FIG. 1C).

EXAMPLE 2

Inducement of Apoptosis by TIP41 Depletion and TRAIL Treatment

<2-1> Analysis of Apoptosis Induced by TIP41 Depletion Using Staining of Nuclear Chromatin The TIP41-repressed cell lines were inoculated with $2\times10^5$ cells/well which was cultured with methods from the experiment example <1-1>, in 6-well plates. After about 24 hours, the cell was treated with TRAIL at 100 ng/ml for 0, 2, 4, 6, 8 hours, and was stained for about 30 minutes using Hoechst 33342 at 5 μg/ml, it in room temperature. The measurement of apoptosis was done by counting the dead cell line with fluorescence microscope after staining chromatin nucleus with Hoechst 33342.

As the result, apoptosis increased in Huh7 cancer cell line treated with both TIP41 siRNA and TRAIL, in comparison to TRAIL-only treatment. The apoptosis increase as the treatment time of TRAIL increases, and as about 30% increase of apoptosis in TIP41 siRNA treated group, in comparison to the control group siRNA treatment, was observed. It indicates that treatment of TIP41 siRNA in Huh7 cancer cell reduces TRAIL resistance (FIG. 2A).

<2-2> Analysis of Apoptosis Induced by TIP41 Depletion using FACS

After reducing the intracellular expression amount of TIP41 by transfecting TIP41 siRNA to Huh7 liver cancer cell line, which was cultured with methods from the experiment example <1-1>, TRAIL was treated at about 100 ng/ml, then apoptosis was stained by separating the dead cell line and normal cell line, with Annexin V-FITc/PI staining method at 0, 2, 4, 6, 8 time period, and FACS (Fluorescent Activated Cell Sorter) was used to measure apoptosis.

In order to measure apoptosis, cell line was collected by using trypsin-EDTA, then FITc-fused annexin v (50 μg/ml) and PI (propidium iodide) (50 ng/ml) were used to stain for about 20 minutes, and FACS Caluber (BD) was used to separate cell line, and then the ratio of annexinV-FITc/PI stained cell line was analyzed.

As the result, the fact that apoptosis occurs after TRAIL treatment with varying time periods was identified through FACS analysis (FIG. 2B), and when TRAIL was treated for about 4 hours with concentrations about 0, 25, 50, 100, 200 ng/ml and same experiment method, increase of apoptosis following the treatment concentration was identified (FIG. 2C).

EXAMPLE 3

Examination of Apoptosis Pathway Induced by TIP41 Depletion and TRAIL Treatment

<3-1> Caspase Activation

After about 72 hours of transfection of TIP41 siRNA in the cultured cell line of the experiment example <1-1>, TRAIL, at about 100 ng/ml, was treated for various time periods. Cell was lysed with lysis buffer [20 mM HEPES (4-(2-hydroxyethyl)-1-piperazineethanesulfonic acid) (pH7.5), 150 mM Nacl, 1 mM EDTA (ethylene diamine tetraacetic acid), 2 mM EGMA (ethylene glycol tetraacetic acid), 1% Triton X-100, 10% glycerol, Protease inhibitor cocktail, phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for about an hour, to stop any nonspecific reaction. After about an hour, the nitrocellulose membrane was reacted for over 12 hours in about 4° C. with 1:1,000 Caspase-3, Caspase-8, Caspase-9 and 1:2,000 PARP (cell signaling technology, USA), then washed with 0.1% TEST (Tris-Buffered Saline Tween-20) for three times, about 10 minutes per washing, and secondary antibody of anti-mouse (Pierce, USA) anti-rabbit (Pierce, USA) were reacted for about an hour in room temperature. Then this was washed for three times with 0.1% TEST, about 10 minutes per washing, and the expression was identified with chemiluminescence reagent.

As the result, FIG. 3A showed that Caspase-9, -8, -3 and PARP are activated by TRAIL treatment at varying time periods after TIP41 depletion. The results indicate that apoptosis by TIP41 depletion increases depending on time and concentration of TRAIL.

<3-2> Release of Cytochrome C in Mitochondria into Cytosol

To figure out whether cytochrome C in mitochondria release to cytosol in order to identify apoptosis pathway, subcellular fractionation and Western Blotting was performed. After reducing the intracellular expression amount of TIP41 by transfecting TIP41 siRNA to Huh7 liver cancer cell line, which was cultured with methods from the experiment example <1-1>, the TIP41-repressed cell lines were inoculated $2\times10^6$ cells/dish in 60 mm dishes. After about 24 hours, TRAIL was treated at about 100 ng/ml for 0, 1, 2, 4 hours, and subcellular fractionation was done. The subcellular fractionation was done by using Subcellular Proteome Extraction kit (Calbiochem Co.); kit consists of 4 buffers, and subcellular fractionation was separates into cytosol, mitochondria, nucleus, and cytoskeleton fraction by using each buffer, respectively.

After adding about 500 μl of the extraction buffer 1 into each cell lines, they were stirred for about 10 minutes at about 4° C., and centrifuged to obtain cellular matrix fraction, and stirring about 500 μl of the extraction buffer for about 30 minutes at about 4° C. and centrifugation obtained mitochondria fraction. The fractionated cytosol and mitochondria were used with Western Blotting method.

After about 72 hours of transfection of TIP41 siRNA in the cultured cell line of the experiment example <1-1>, TRAIL was treated for 0, 2, 4 and 6 hours. Cell was lysed with lysis buffer [20 mM HEPES (4-(2-hydroxyethyl)-1-piperazineethanesulfonic acid) (pH7.5), 150 mM Nacl, 1 mM EDTA (ethylene diamine tetraacetic acid), 2 mM EGMA (ethylene glycol tetraacetic acid), 1% Triton X-100, 10% glycerol, Protease inhibitor cocktail, phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for about an hour, to stop any nonspecific reaction. Tubulin was used as cytosolic fraction marker, and Peroxiredoxin III was used for mitochondria. After about an hour, the nitrocellulose membrane was reacted for over 12 hours in about 4° C. with 1:1,000 Cytochrome C (BD, USA), 1:5,000 Tubulin (Sigma Aldrich, USA) and 1:2, 000 Peroxiredoxin III (Abfrontier, Korea) then washed with 0.1% TEST (Tris-Buffered Saline Tween-20) for three times, about 10 minutes per washing, and secondary antibody of anti-mouse (Pierce, USA) anti-rabbit (Pierce, USA) were reacted for an hour in room temperature with 1:2,000 ratio. Then this was washed for three times with 0.1% TEST, about 10 minutes per washing, and the expression was examined with chemiluminescence reagent.

As the result, it was founded that Cytochrome C release to cytosol after treating TIP41 siRNA (FIG. 3B). Hence, Caspase-8 and -9 were activated, and cytochrome C from mitochondrion to cytosol was released. From these results, it was confirmed that apoptosis occurs via mitochondria. These findings indicate that apoptosis induced by TIP41 depletion and TRAIL treatment in Huh7 liver cancer cell line is closely associated with a caspase/mitochondria-dependent apoptotic cell death pathway.

EXAMPLE 4

Activation of JNK Pathway by TIP41 Depletion and TRAIL Treatment

<4-1> JNK Activation by TIP41 Depletion and TRAIL Treatment

The JNK pathway has been reported to regulate cell death by TRAIL. and

Activation of JNK and p38 has been reported to induce apoptosis. In order to find out apoptosis induced by TRAIL treatment and TIP41 depletion, which is identified in the <Example>, and Mitogen-Activated Protein (MAP) pathway, in particular the relationship between JNK and p38, Huh7 liver cancer cell line was transfected with TIP41 siRNA and than treated with TRAIL (100 ng/ml) at 0, 1, 2, 4 hours. Relationship between apoptosis induced by TIP41 protein depletion and TRAIL treatment and JNK as well as p38 was examined using Western Blotting. After about 72 hours of transfection of TIP41 siRNA in the cultured cell line of the experiment example <1-1>, TRAIL was treated for about 0, 2, 4 and 6 hours. Cell was lysed with lysis buffer [20 mM HEPES (4-(2-hydroxyethyl)-1-piperazineethanesulfonic acid) (pH7.5), 150 mM Nacl, 1 mM EDTA (ethylene diamine tetraacetic acid), 2 mM EGMA (ethylene glycol tetraacetic acid), 1% Triton X-100, 10% glycerol, Protease inhibitor cocktail, phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for about an hour, to stop any nonspecific reaction. After about an hour, the nitrocellulose membrane was reacted for over 12 hours in about 4° C. with 1:1,000 ratio p-MKK7 (cST Inc., USA), p-p38 (cST Inc., USA), 1:1,000 ratio p-JNK (cST Inc., USA), and 1:5,000 ratio Tubulin (Sigma Aldrich, USA), then washed with 0.1% TEST for three times, about 10 minutes per washing, and secondary antibody of anti-mouse (Pierce, USA) anti-rabbit (Pierce, USA) were reacted for about an hour in room temperature with 1:2,000 ratio. Then this was washed for three times with 0.1% TEST, about 10 minutes per washing, and the expression was examined with chemiluminescence reagent.

As shown in FIG. 4A, down-regulation of TIP41 by RNAi is sufficient to prolong TRAIL-induced MKK7/JNK activation (FIG. 4A).

<4-2> Reduction of Apoptotic Cell Death by Treatment of JNK Inhibitor

In order to find relationship between JNK transduction pathway and apoptosis induced by TRAIL treatment and TIP41 depletion, after cell line was incubated with same method as experiment example <4-1>, and the cell line was treated with TIP41 siRNA and then treated with SP600125 (10 μg/ml), a JNK repressor for 1 hour to inhibit JNK transduction pathway. The apoptosis induced with TRAIL stimulus was measured with FACS analysis using Annexin-FITc/PI staining method.

As the result, in the experiment treating TRAIL after inhibiting JNK transduction pathway by treating JNK repressor, apoptosis was reduced. Through this, the fact that JNK transduction pathway is serving an important role in apoptosis induced by TRAIL treatment and TIP41 protein depletion was identified (FIG. 4B).

EXAMPLE 5

Confirmation of p53 Independent Apoptosis Pathway After Depletion of TIP41 Protein <5-1> Confirmation of p53 Independent Apoptosis Pathway in Liver Cancer Cell Line The largest problem of anticancer agents that are being used is the side-effect of killing normal cell lines, not being able to differentiate between normal and cancer cell lines, and the mechanism of normal cell line apoptosis is known to be occurring via activation of p53 pathway. Since anticancer agent that induces p53 dependent apoptosis influences both cancer and normal cell line, it was identified whether TRAIL-induced apoptosis after TIP41 siRNA treatment occurs via p53. After about 72 hours of transfection of TIP41 siRNA into HCT 1116 p53 wild type and p53 null type, colon cancer cell lines, about 100 ng/ml TRAIL was treated at 0, 2, 4 and 6 hours. In order to identify whether apoptosis occurs via p53 transduction pathway by performing Western Blotting using phospho-p53 antibody, antibody that identifies phosphorylation of p53 was used. Using p-p53 (Ser 6), p-p53 (Ser 9), p-p53 (Ser 15), p-p53 (Ser 20), p-p53 (Ser 37), p-p53 (Ser 46) and p-p53 (Ser 392), phosphorylation of p53 serine 6, 9, 15, 20, 37, 46, 392 was examined.

Cells were lysed with lysis buffer [20 mM HEPES (4-(2-hydroxyethyl)-1-piperazineethanesulfonic acid) (pH7.5), 150 mM Nacl, 1 mM EDTA (ethylene diamine tetraacetic acid), 2 mM EGMA (ethylene glycol tetraacetic acid), 1% Triton X-100, 10% glycerol, Protease inhibitor cocktail, phosphatase inhibitor cocktail I/II], cell debris was removed by centrifuging in about 15,000 rpm for about 10 minutes and protein was collected. After proteins were separated depending on molecular weights through SDS-PAGE, the separated protein was transferred to nitrocellulose membrane, and was blocked with about 5% skim milk for about an hour, to stop any nonspecific reaction. After about an hour, the nitrocellulose membrane was reacted for over 12 hours in about 4° C. with 1:1,000 ratio p-p53 (Ser 6), p-p53 (Ser 9), p-p53 (Ser 15), p-p53 (Ser 20), p-p53 (Ser 37), p-p53 (Ser 46) and p-p53 (Ser 392) (cST Inc, USA), then washed with 0.1% TEST for three times, about 10 minutes per washing, and secondary antibody of anti-mouse (Pierce, USA) anti-rabbit (Pierce, USA) were reacted for about an hour in room temperature with 1:2,000 ratio. Then this was washed for three times with 0.1% TEST, about 10 minutes per washing, and the expression was identified with chemiluminescence reagent.

As the result, when cells were treated with TIP41 siRNA and TRAIL treatment, phosphorylation at Ser 15 and 392 of p53 protein was identified (FIG. 5A). The phosphorylation of Ser 15 occurs by activation of ATM (Ataxia telangiectasia mutated)/ATR (ATM and RAD3-related) pathway, which influences apoptosis due to DNA damage, and DNA-dependent protein kinase (DNA-PK) and its relationship with apoptosis is known, and phosphorylation of Ser 392 is known to influence p53 protein's binding to DNA sequence in nucleus. Hence, there is a possibility that TRAIL-mediated apoptosis through TIP41 depletion is p53-dependent. However, considering the result of non-expression of serine activated with JNK transduction pathway, its potential of p53-independent could not have been omitted.

<5-2> p53-Deficient Cell Line Culture

HCT116 cell line is a colorectal cancer cell line that produces p53 protein normally, and it is known to be a TRAIL-resistant cell line that does not run into apoptosis frequently by TRAIL treatment. The HCT116 p53-deficient cell line was established in 1998 by Dr. B. Vogelstein, with p53 gene deficit (Vogelstein, B., Science, 1998). The cell line was distributed for the experiment, and the cell lines were subcultured with 3-day period, in DMEM (Hyclone, USA) medium with about 10% bovine fetal serum, about 100 mg/ml streptomycin, and about 100 IU/ml ampicillin, added with about 100 µg/ml G418 stable marker antibiotics.

<5-3> Confirmation of p53-Independent Apoptosis Pathway in p53 Null Cell Line

In order to identify p53-independent possibility, TIP41 siRNA was transfected into HCT116 p53 null cell line, which was produced in experiment example <5-2>, and TRAIL was treated with same conditions to induce apoptosis, and then FACS analysis using Annexin-FITc/PI staining method was performed.

As the result, when TRAIL was treated after TIP41 siRNA transfection, apoptosis was induced well in HCT116 p53-deficient cell line, as well as Huh7 liver cancer cell line, which indicates that TIP41 depletion and TRAIL treatment induces apoptosis of cancer cell lines in a p53-independent pathway Therefore, activation of p53 Ser 15 shown in FIG. 5A has less influence in TRAIL-mediated apoptosis by TIP41 depletion, and it is expected that p53 moves to nucleus to enhance transcription activity (FIG. 5B).

EXAMPLE 6

Measurement of TRAIL Receptor Expression Level

<6-1> Confirmation of TRAIL Receptor Expression in Various Cell Line

A research has been reported that enhancement of TRAIL receptor expression is done as a method of increasing cancer cell line apoptosis, in order to enhance the effect as a cancer cell line specific cure by overcoming TRAIL resistance. In relation to this research, To determine the relationship between TIP41 depletion and TRAIL receptors, the expression level of TRAIL was identified in normal, liver cancer and lung cancer cell lines. There are four types of TRAIL receptor, which are TRAIL-R1 (DR4), TRAIL-R2 (DR5), TRAIL-R3 (DcR1), TRAIL-R4 (DcR2); R1 and R2 function as apoptosis receptors, inducing the cell lines to run apoptosis when TRAIL is bound, but R3 and R4 are known as decoy receptors, reducing TRAIL-induced apoptosis by inhibiting binding of TRAIL to R1 and R2.

Real-time quantitative PCR was done by extracting RNA from Huh7 liver cancer cell line, HAEC (Human aortic endothelial cell, clonetics) normal cell line, and A549 lung cancer cell line (Korean Cell Line Bank) using Trizol, and cDNA was synthesized by using about 1 µg of the extracted RNA with reverse transcriptase superscript II (invitrogen), and based on this template, the primers of TIP41, TRAIL-R1 (Death receptor (DR)$_4$), TRAIL-R2 (DR5), TRAIL-R3 (DcR1) and TRAIL-R4 (DcR2) genes were used. The relative expression level of each gene was identified via PCR result with 2-DDct comparative method. TIP41 forward primer (SEQ. ID. NO: 3: 5'-att gaa agc cag aga aca ga-3') and TIP41 reverse primer (SEQ. ID. NO: 4: 5'-tct cgt gtc att cat tct ga-3'), DR4 forward primer (SEQ. ID. NO: 5: 5'-ctc agc gga atc aat cag ctg tg-3'), DR4 reverse primer (SEQ. ID. NO: 6: 5'-aga gga aca cga caa tca gcc tta g-3'), DR5 forward primer (SEQ. ID. NO: 7: 5'-atc aag cgg ccc cct ttt ttt cac-3'), DR5 reverse primer (SEQ. ID. NO: 8: 5'-ctc att gtc aca ctc ctc gac agc-3'), DcR1 forward primer (SEQ. ID. NO: 9: 5'-tcc cca aga ccc taa agt tc-3'), DcR1 reverse primer (SEQ. ID. NO: 10: 5'-ggc acc aaa ttc ttc aac ac-3'), DcR2 forward primer (SEQ. ID. NO: 11: 5'-gca cag agg gtg tgg att ac-3') and DcR2 reverse primer (SEQ. ID. NO: 12: 5'-gag cag atg cct ttg agg ta-3') were used for Real-time quantitative PCR. At the time, the primer pair written as forward primer (SEQ. ID. NO: 13: 5'-ctc gct ccg tgg cct tag-3') and reverse primer (SEQ. ID. NO: 14: 5'-caa atg cgg cat ctt caa-3') of beta-2-microglobulin (B2M) was used as a quantitative control group, which was also run Real-time quantitative PCR. The conditions of the PCR include about 10 minutes of denaturation at about 95° C., and about 40 cycles with conditions of about 30 seconds at about 95° C., about 30 seconds at about 60° C., and about 1 minute at about 72° C.; afterwards, it was elongated for about 8 minutes at about 72° C., and was cooled to room temperature. The result of Real-time quantitative PCR was analyzed with 2-DDct comparison method, which compensates expression level of each sample's TRAIL receptor into B2M expression level, and afterwards the multiples of expression level in liver cancer tissue to TRAIL receptor expression level in normal liver tissue was shown in FIG. 6 as a graph.

As the result, TRAIL-R3 (DcR1) was less expressed in liver and lung cancer cell line, TRAIL resistant cancer cell line, compared to normal cell line, and TRAIL-R4 (DcR2) was expressed at similar level compared to normal cell line. TRAIL-R1 (DR4) had slightly higher expression level in liver and lung cancer cell line, compared to normal cell line, but its overall expression level was low, and over-expression of TRAIL-R2 (DR5) in liver and lung cancer cell line, compared to normal cell line, was identified. Hence, as it is generally known, the apoptosis receptor is more expressed in liver and lung cancer cell line, which indicates that there is no correlation between TRAIL resistance and expression of the receptor (FIG. 6A).

<6-2> Confirmation of TRAIL Receptor Expression by TRAIL Treatment and TIP41 Depletion In order to find relationship between apoptosis induced by knockdown of TIP41 protein and TRAIL receptor, expression level of TRAIL receptors in Huh7 liver cancer cell line treated with TRAIL and TIP41 siRNA was examined. After about 72 hours of transfection of TIP41 siRNA into Huh7 liver cancer cell line, about 100 ng/ml TRAIL was treated for 4 and 6 hours. After treatment of TRAIL, Real-time quantitative PCR was done by extracting RNA from Huh7 liver cancer cell line using Trizol, and cDNA was synthesized by using about 1 µg of the extracted RNA with reverse transcriptase superscript II (invitrogen), and based on this template, the primers of TIP41, TRAIL-R1 (Death receptor (DR)$_4$), TRAIL-R2 (DR5), TRAIL-R3 (DcR1) and TRAIL-R4 (DcR2) genes were used. The relative expression level of each gene was calculated via PCR result with 2-DDct comparative method.

As shown in FIG. 6B, when TIP41 siRNA transfected group and control group were compared, it was founded that there was no significant difference of expression of TRAIL receptors (TRAIL-R1, -R2, -R3 and -R4) after depletion of TIP41 protein (FIG. 6B).

<6-3> Confirmation of TRAIL Receptor Expression for Liver Cancer Tissues

The expression level of TRAIL receptor was measured at liver cancer tissue and adjacent tissues with Reverse Transcriptase-PCR. The tissues used in the experiment were collected with patients agreement before surgeries in Catholic University of Medicine in Seoul, Korea; 19 tissues, including hepatocellular carcinoma and nearby normal tissues, were collected from patients of each liver cancer stages, including I (n=5), II (n=5), III (n=5) and IV (n=4), classified with Edmonson and Steiner classification method.

Real-time quantitative PCR was done by extracting RNA from Huh7 liver cancer cell line using Trizol, and cDNA was synthesized by using about 1 μg of the extracted RNA with reverse transcriptase superscript II (invitrogen), and based on this template, the primers of TIP41, TRAIL-R1 (Death receptor $(DR)_4$), TRAIL-R2 (DR5), TRAIL-R3 (DcR1) and TRAIL-R4 (DcR2) genes were used. The relative expression level of each gene was identified via PCR result with 2-DDct comparative method.

As the result, a significant increase of expression level of TRAIL-R1 (DR4) was observed the most at liver cancer stage I, and stage III, II, IV followed respectively; the difference of expression level was significant. As for TRAIL-R2 (DR5), it was observed that its expression significantly increases in liver cancer tissue at stage I and stage V when compared with normal tissue, but expression level of TRAIL-R3 (DcR1) was very low at almost every stage, and there was no difference observed between normal and liver cancer tissue. Moreover, it was observed that TRAIL-R4 (DcR2) expression significantly increases only at stage II in liver cancer tissue; in other stages, the expression level was similar with normal tissue, or even showing higher expression level in normal tissue (FIG. 6C).

EXAMPLE 7

Examination of Apoptosis in Normal Cell Line

<7-1> Apoptosis Analysis in Normal Cell Line by TIP41 Depletion and TRAIL Treatment Using FACS Analysis TIP41 is specifically over-expressed in cancer cell line, but it is also expressed in normal cell line; since TIP41 depletion can induce apoptosis of normal cell line, as it occurs in cancer cell line, apoptosis was induced in HAEC, a normal cell line, with TIP41 protein depletion and TRAIL treatment, in order to identify whether apoptosis induced by TIP41 depletion and TRAIL treatment is a reaction specific to cancer cell line.

After about 72 hours of transfection of TIP41 siRNA into HAEC normal cell line, about 100 ng/ml TRAIL was treated for 0, 2, 4 and 6 hours, to induce apoptosis. The cell death was analyzed using Annexin V-FITc/PI staining method as the methods mentioned above, and FACS (Fluorescent Activated Cell Sorter) was used to measure apoptosis.

As the result, it was founded that there is no difference in apoptosis, whether TIP41 siRNA was treated after TRAIL treatment or not. Therefore, the apoptosis induced by TRAIL treatment after transfection of TIP41 siRNA that is over-expressed specifically in cancer cell line, occurs specifically in cancer cell line (FIG. 7A).

<7-2> Analysis of Pro-Apoptotic Proteins in Normal Cell Line by Depletion of TIP41 and TRAIL Treatment TIP41 siRNA was transfected into normal cell line with same experiment method, activation of caspase-8, -3, JNK, PARP proteins was examined. Normal cell lines were treated with 100 ng/ml TRAIL for 0, 2, 4 hours, and then expression and activation of pro-apoptotic proteins were examined using western Blotting method, as mentioned above.

As the result, the depletion of TIP41 protein after transfection of TIP41 siRNA was identified, but there was no change identified for Caspase-8, -3, JNK, and pJNK (phosphorylation JNK), which influence apoptosis transduction pathway. Also, by identifying their non-activation of these proteins, it was confirmed that apoptosis induced by transfection of TIP41 siRNA and TRAIL occurs specifically in cancer cell line (FIG. 7B).

EXAMPLE 8

TRAIL-Mediated Apoptosis Through TIP41 Depletion in Cancer Cell Line

<8-1> TRAIL-Mediated Apoptosis Through TIP41 Depletion in Lung Cancer Cell Line

<8-1-1> Confirmation of Apoptosis in Lung Cancer Cell Lines Induced by TIP41 Protein Depletion by Western Blot In order to prove the function as a sensitizer that overcomes TRAIL resistance due to TIP41 protein depletion in TRAIL-resistant cancer cell line, other than liver cancer cell line used in the <Example>, after about 72 hours of transfection of TIP41 siRNA with same methods as that of liver cancer cell line into A549 cell line, a lung cancer cell line, about 100 ng/ml TRAIL was treated for 0, 1, 2, 3, and 4 hours, and activation of proteins related with apoptosis was examined using Western Blot.

As the result, as shown in the liver cell line, apoptosis was identified by activation of JNK, Caspase-8 and PARP, although weaker than that of liver cancer (FIG. 8A).

<8-1-2> Confirmation of Apoptosis in Lung Cancer Cell Lines Induced by TIP41 Protein Depletion Using Nuclear Chromatin Staining A549 cell line, lung cancer cell line, was transfected with TIP41 siRNA to deplete the expression level of TIP41 in cells, and treated with 100 ng/ml of TRAIL, and the apoptosis rates were measured using nuclear chromatin staining at 0, 1, 2, 4, 6 hours respectively.

Cells were stained by Hoechst 33342 and the apoptosis was counted by fluorescence microscope. TIP41 depleted cell lines were seeded into $2 \times 10^5$ cells/well with 6 well plates.

After 24 hours, the cells were treated with 100 ng/ml TRAIL for 0, 1, 2, 4, 6 hours, respectively, and then stained with 5 μg/ml of Hoechst 33342 for 30 minutes at room temperature. The nuclear stained cells were observed under fluorescence microscope and the number of dead cells was counted to measure the apoptosis rate.

The result is illustrated in FIG. 8B-A, which shows that the apoptosis was increased when A549 lung cancer cell lines was treated with TIP41 siRNA and TRAIL, compared to a case of cell lines treated with TRAIL alone. The observation also indicated that the longer the TRAIL was treated, the more the apoptosis was increased. Further, the apoptosis was increased approximately by 30% more in TIP41 siRNA treated group compared to the control group treated with siRNA. Therefore, it was confirmed that TIP41 siRNA of A549 lung cancer cell lines reduces the resistance to TRAIL (FIG. 8B-A).

<8-1-3> Confirmation of TRAIL-Mediated Apoptotic Cell Death Through TIP41 Depletion in Lung Cancer Cells by FACS analysis A549 cells were transfected with TIP41 siRNA to deplete expression level of TIP41 in cells, treated with 100 ng/ml of TRAIL, and stained by Annexin V-FITC/PI staining at 0, 1, 2, 4, 6 hours differently for death cell lines and normal cell lines, and the apoptosis was measured using FACS (Fluorescent activated cell sorter).

To measure the apoptosis, cells were trypsinized using trypsin-EDTA, stained with FITC conjugated annexin v (50 μg/ml) and PI(propidium iodide) (50 ng/ml) for 20 minutes, and then analyzed with FACS Calibur(BD) to analyze the ratio of cells stained with annexin V-FITC/PI.

Compared to the case in which A549 cells (i.e., lung cancer cell line) with the control siRNA, the case of the present invention in which cells were treated with TIP41 siRNA exhibited noticeable increase of apoptosis of A549 cells (FIG. 8B-B). Further, as illustrated in FIG. 8B-C, the TRAIL was treated at concentration of 0, 25, 50, 100, and 200 ng/ml for 4 hours to examine the apoptosis. As a result, it was observed that the higher concentration of TRAIL in the example of treating with both TRAIL and TIP41 siRNA increased apoptosis (FIG. 8B-C).

Based on the above results, it was confirmed that TIP41 siRNA of the present invention decreases the resistance of lung cancer cell line to TRAIL, and induces cancer specific apoptosis.

<8-2> TRAIL-Mediated Apoptosis in Colorectal Cancer Cell Line Through TIP41 Depletion After about 72 hours of transfection of TIP41 siRNA with same methods into HCT116 colorectal cancer cell line, about 0, 50 and 100 ng/ml TRAIL was treated, and 0.3% DMSO was treated as the vehicle, and experiment inducing apoptosis was performed. The dead cells were stained with Annexin V-FITC/PI staining method as the methods mentioned above, and FACS was used to measure cell death.

As the result, increase of apoptosis proportional to TRAIL treatment concentration was identified; increase of apoptosis in TIP41 siRNA transfected group compared to control group was also identified. Hence, by identifying apoptosis in colorectal cancer cell line as in liver cancer cell line, it was identified that Inhibitors for TIP41 proteins could be used as a TRAIL sensitizer for TRAIL-resistant cancer (FIG. 8A-B).

<8-3> TRAIL-Mediated Apoptosis in Liver Cancer Cell Lines by TIP41 Depletion

To investigate a function as a sensitizer to overcome TRAIL resistance of the TRAIL-resistant cancer cell lines other than Huh liver cancer cell line used in the above <Example> due to inhibition of TIP41 protein expression, HepG2 (liver hepatocellular cells) and SK-Hep1 cell were transfected with TIP41 siRNA, and after 72 hours, treated with 100 ng/ml of TRAIL for 0, 1, 2, 4, 6 hours respectively, and activation of proteins related to apoptosis were measured by Western blot.

As illustrated in FIGS. 8C-A and 8C-B, it was confirmed that HepG2 and SK-Hep1 cells had activation of Caspase-8 and PARP by TIP41 siRNA to cause apoptosis (FIG. 8C-A and 8C-B).

EXAMPLE 9

Confirmation of TIP41 Function Through Animal Experiment

<9-1> Transplanting of Huh7 Liver Cancer Cell Line into Nude Mouse

After xenograft approximately $2 \times 10^6$ Huh7 liver cancer cells into right back region of nude mouse, the tumor was grown into a certain size (50-100 mm3). The experiment was performed with 7 mice per group (n=7); 28 nude mice in total were purchased from Japan SLc Inc.

<9-2> Measurement of Tumor Size Change by TIP41 Depletion and TRAIL Treatment

After forming tumors by transplanting the Huh7 liver cancer cell line into nude mouse as the method mentioned in experiment example <9-1>, control siRNA and TIP41 siRNA were injected into the tumor on 0, 4, 6, and 8th days during 12 days period, and TRAIL was injected on 2, 5, 7, 9, 10, and 11th day, and the mouse was sacrificed on 12th day. Lipofectamine RNAiMax reagent, at 50 nM concentration, was used to make a pharmaceutical composition and was injected into the tumor; after injecting about 2.5 μg/kg of TRAIL on 2, 5, 7, 9, 10, and 11th day, the size of tumor following TIP41 siRNA and TRAIL treatment was to be observed after separating the group into four different groups (control siRNA+vehicle, control siRNA+TRAIL, TIP41 siRNA+vehicle, TIP41 siRNA+TRAIL).

As the result, the decrease of tumor size was observed in the group with TIP41 siRNA injection, compared to that of control siRNA, and when TRAIL was injected, the size of tumor decreased even more in case of TIP41 siRNA treatment, compared to control siRNA (FIG. 9A).

<9-3> Observation of Apoptosis in Cancer Tissue

The mice were separated into groups of without siRNA treatment, control siRNA treatment and siRNA with TRAIL treatment and without treatment; the tumors were excised from the groups, fixed in formalin, and were embedded in paraffin. After making sections with about 5 an thickness, xylene was used to remove paraffin, and was rehydrated following ethanol concentration. 4% praformaldehyde solution was treated to fix the tissue section, Proteinase K solution was treated to make the tissue transparent, and after fixing it in 4% paraformaldehyde solution again, TUNEL staining kit (promega, USA) was used to perform the experiment. While equilibrating the tissue section using equilibration buffer, rTdT reaction solution was prepared and was treated in equilibrated region. Finally, streptavidin HRP solution was treated, and color reaction was done using DAP mixture, and then optic microscope was used for observation.

As the result, a significant increase of apoptosis in the group with TIP41 siRNA and TRAIL treated group was observed (FIG. 6B).

<9-4> Measurement of Tumor Apoptosis

After extracting proteins by lysing the tumors collected from four groups (control siRNA+vehicle, control siRNA+TRAIL, TIP41 siRNA+vehicle, TIP41 siRNA+TRAIL), using Caspase-8 antibody, a marker of apoptosis, the apoptosis was examined by Western Blotting method.

As the result, the effect of TIP41 siRNA was identified by the decrease of TIP41 protein expression level, and the increase of caspase-8 expression after TIP41 siRNA transfection, which did not increase by TRAIL treatment, was observed. Through this, it was identified that TIP41 siRNA can be applied in vivo, and may be used as an anticancer agent that has an effect of overcoming TRAIL resistance by inducing apoptosis effectively for the TRAIL-resistant cancers (FIG. 9C).

EXAMPLE 10

Measurement of Binding Between TIP41 and PP2Ac

<10-1> Construction of Expression Vector

In order to produce vectors that express TIP41, PP2Ac, MKK7, alpha4 and PR65 genes, RNA was extracted from liver cancer cell and cloned into expression vector. Using the reversed RNA as a template, PCR was performed using primers that are corresponded to each gene. PCR was performed using TIP41 forward primer (SEQ. ID. NO: 15: 5'-cg ggt acc aa atg atg atc cac ggc ttc'-3') and TIP41 reverse primer (SEQ. ID. NO: 16: 5'-ccc gga tcc tta ttc Cac ttg tgt act-3'), PP2Ac forward primer (SEQ. ID. NO: 17: 5'-cg gga tcc atg gac gag aag gtg ttc-3'), PP2Ac reverse primer (SEQ. ID. NO: 18: 5'-a tag ttt agc ggc cgc tta cag gaa gta gtc tgg-3'), MKK7 forward primer (SEQ. ID. NO: 19: 5'-ccg ctc gag atg gcg gcg tcc tcc ctg-3'), MKK7 reverse primer (SEQ. ID. NO: 20: 5'-gg ggt acc cct gaa gaa ggg cag gtg-3'), alpha4 forward primer (SEQ. ID. NO: 21: 5'-cg gga tcc atg gct gct gag gac gag-3'), alpha4 reverse primer (SEQ. ID. NO: 22: 5'-a tag ttt agc ggc cgc tca gcc cat gtt ctg tcg-3'), PR65 forward primer (SEQ. ID. NO: 23: 5'-cg gga tcc atg gcg gcg gcc gac ggc-3') and PR65 reverse primer (SEQ. ID. NO: 24: 5'-a tag ttt agc ggc cgc tca ggc gag aga cag aac-3'). The conditions of PCR are the followings; 3 minutes of denaturation at 95° C., and 30 cycles with conditions of one minute at 95° C., one minute at 58° C., and 1 minute and 30 seconds at 72° C.; at the end of cycles, it was elongated for about 10 minutes at 72° C., and was cooled to 4° C.

For vector for TIP41, extracted PCR product was cut with KpnI and BamHI restriction enzymes, and then was inserted into pHA vector (pcDNA3.1; vector is produced by Invitrogen Co. via the insertion of HA tag). The used primer includes KpnI and BamHI restriction sites. For PP2Ac, PR65, MKK7, and alpha4, amplification using primer that includes Not I and BamHI restriction site was done; the PCR product was purified, then excised with Not I and BamHI restriction enzyme, and was inserted into pGST vector (pEBG vector) (Mayer et al. 1995 Current Biology 5 (3):296-305. Also, in order to produce recombination protein, PCR was done using same primer mentioned above. PCR products for MKK7 and PP2Ac were inserted into pET21a (Novagen Inc.) vector, which is an *E. coli* expression vector, respectively, and PCR product for TIP41 was inserted into pGEX4T-1 (GE helthcare) vector. By the process, pET21-MKK7, pET21-PP2Ac, and pGEX4T-TIP41 were constructed.

<10-2> Cultivation of HEK293T Cell Line

The HEK293T cell line, distributed from Korean Cell Line Bank, was cultured in Dulbecco's modified eagle's medium (DMEM) with 10% fetal bovine serum included, with about 37° C. 5% $CO_2$. In order to transfect siRNA, HEK293T cell line was planted in $1\times10^6$ cells/100 mm dish and cultured for about 24 hours; transfection was done afterwards.

<10-3> Confirmation of Binding Between TIP41 and PP2Ac

The inventors revealed through the experiment that cause of apoptosis by TIP41 depletion and TRAIL treatment is the result of continuous activation of JNK, which means that TIP41 depletion induces JNK activation mechanism. In order to identify whether JNK activation is controlled by the protein that is known to bind with TIP41, the expression vector that expresses Protein Phosphatase 2Ac (PP2Ac), a protein known to bind with TIP41 in a recent report, was manufactured in the experiment example <10-1>.

PP2Ac protein is a Serine/Threonine phospatase that performs function of removing phosphate that is phosphorylated in many proteins Ser/Thr amino acid. Foxo1, NF-kappaB (p65), AMPK, and MKK4 are known to be substrates of PP2Ac protein.

In order to identify the binding of TIP41 with PP2Ac, $2\times10^5$ HEK293T cell line was seeded in 100 mm culture dish and PP2Ac was over-expressed by transfecting PP2Ac expression vector, manufactured from experiment example <10-1>, into the cell by using Lipofectamine LTX reagent. The cell lysate was extracted from the transfected cell and GST-Pull down analysis was performed. GST-pull down analysis is done by adding 40 µl GSH-bead into 1 mg/ml cell lysate, and after carefully stirring for about 12 hours in about 4° C., about 1 ml PBST[0.1% Tween20 included PBS] buffer was added for washing, and the procedure was repeated for 6 times. At the end, 100 µl 1× sample buffer (for Western Blotting) was added into the washed bead, then it was boiled for about 5 minutes in about 95° C. heating block, and was cooled on ice for about 2 minutes. Afterwards, Western Blotting was performed as the condition mentioned above, using each antibody.

As the result, as shown in FIG. 10A, it was identified that TIP41 binds with PP2Ac, as alpha 4, which was provided as the positive control group. Also, each expression vector s expression level was identified by the whole cell lysate (WcL) before GST pull down (FIG. 10A).

<10-4> Confirmation of Interaction Between TIP41 and PP2Ac Complex

In order to identify the binding between TIP41 and PP2Ac, known to be a JNK kinase, the expression vector produced in experiment example <10-1> was transfected into HEK293T cell line as the previous method and Western Blotting was performed after GST-Pull down.

As the result, as shown in FIG. 10B, binding of TIP41 and PP2Ac, hence binding of PP2Ac, PR65 and alpha 4 was identified (FIG. 10B).

EXAMPLE 11

Confirmation of Interaction Between TIP41 and MKK7

<11-1> Confirmation of Interaction Between TIP41 and MKK7 after MKK7 Over-Expression In order to identify the binding between TIP41 and MKK7, known to be a JNK kinase, the expression vector produced in the <Example 10> was transfected into HEK293T cell line as the same method and over-expressed, then GST-Pull down was performed.

As the result, as shown in FIG. 11A, binding of TIP41 and MKK7 was identified (FIG. 11A).

<11-2> Confirmation of Interaction Between TIP41 and MKK7 using Immunoprecipitation In order to identify interaction between TIP41 and MKK7, each antibody was used to perform immunoprecipitation, and binding between TIP41 and MKK7 was identified with Western Blotting. Immunoprecipitation is done by adding about 2 µg antibody of protein to be precipitated into 1 mg cell lysate and reacted for about 2 hours in about 4° C., and add about 30 µl Protein G sepharose bead into each and react for about 12 hours in about 4° C. Afterwards, about 1 ml PBST[0.1% Tween20 included PBS] buffer was added for washing, and the procedure was repeated for about 4 times. Then 100 µl 1× sample buffer (for Western Blotting) was added into the washed bead, and then it was boiled for about 5 minutes in about 95° C. heating block, and was cooled in ice for about 2 minutes. Afterwards, Western Blotting was performed using MKK7 and TIP41 antibody.

As the result, as shown in FIG. 11B, binding of TIP41 with MKK7 was identified (FIG. 11B).

EXAMPLE 12

Confirmation of Interaction Between TIP41 and PP2Ac or Between TIP41 and MKK7

In order to identify interaction among TIP41 and PP2Ac and MKK7 more accurately, GST-pull down analysis was performed with 1:1 reaction ratio of recombination protein synthesized in *E. coli*, not for the intracellular interaction between TIP41 and MKK7. The recombination protein was produced by transfecting the *E. coli* expression vectors synthesized in the experiment example <10-1> into BL21 *E. coli* strain. The inducement was done by inoculating the transfected *E. coli* into LB Broth and was cultured until 0.4-0.6 OD level, then added Isopropyl β-D-1-thiogalactopyranoside, IPTG with a final concentration of 1 mM and cultivated in 30° C. for 2 h. And then, lysate was prepared by using sonication, and was used for GST-pull down.

As the result, as shown in FIG. 11C, direct interaction of TIP41 and MKK7 was identified, and direct interaction of TIP41 and PP2Ac was also identified (FIG. 11C).

Also, the interaction among TIP41 and PP2Ac and MKK7 was identified in the result performed in experiment example <10-4> (FIG. 10B).

EXAMPLE 13

Identification of Binding Site of TIP41 that Binds with MKK7

In order to identify the binding site of TIP41 that binds with MKK7, TIP41 fragment expression vectors were cloned as previously mentioned in the <Example 10>.

As shown in FIG. 12A, full length TIP41 was divided into 6 fragments, D1~D6, and, using the following primer, each fragment was amplified and inserted into pHA expression vector. TIP41-D1 forward primer (SEQ. ID. NO: 15), TIP41-D1 reverse primer (SEQ. ID. NO: 25: 5'-cg gga tcc cag gct tga aac tcc atg-3'), TIP41-D2 forward primer (SEQ. ID. NO: 15), TIP41-D2 reverse primer (SEQ. ID. NO: 26: 5'-cg gga tcc g gaa ggt gga aca tgc atc-3'), TIP41-D3 forward primer (SEQ. ID. NO: 27: 5'-gg ggt acc atg ctt aaa gtg gcc tgt g-3'), TIP41-D3 reverse primer (SEQ. ID. NO: 16), TIP41-D4 forward primer (SEQ. ID. NO: 28: 5'-cg gga tcc atg ctt aaa gtg gcc tgt-3'), TIP41-D4 reverse primer (SEQ. ID. NO: 29: 5'-ccg ctc gag cag gct tga aac tcc atg-3'), TIP41-D5 forward primer (SEQ. ID. NO: 15), and TIP41-D5 reverse primer (SEQ. ID. NO: 30: 5'-cg gga tcc gtg ttc acc ctc cgt cct-3'), TIP41-D6 forward primer (SEQ. ID. NO: 31: 5'-cg gga tcc aaa ttg aaa gcc aga gaa c-3') and TIP41-D6 reverse primer (SEQ. ID. NO: 16) were used to perform PCR.

In order to over-express the vectors that express TIP41 fragments of D1~D6, 3×106 HEK293T cell line was planted in 100 mm culture dish and the cloned TIP41 D1~D6 fragment expression vectors were transfected into cell by using Lipofectamine LTX reagent. The cell lysate was extracted from the transfected cell and GST-Pull down analysis was performed. The GST-pull down analysis was performed as mentioned previously.

FIG. 12 B shows that the fragments binding with MKK7 were full length TIP41 protein, and fragment D3 and D6, repectively. Thus, it was identified that MKK7 binds into N terminal region of the reported TIP41 protein (SEQ. ID. NO: 1) to site 230-272 (FIG. 12).

EXAMPLE 14

Identification of Binding Site of MKK7 that Binds with TIP41

In order to identify the binding site of MKK7 that binds with TIP41, the MKK7 fragment expression vectors were cloned using the method as previously mentioned in <Example 10>. MKK7-D1 forward primer (SEQ. ID. NO: 32: 5'-cg gga tcc cgc agc atg gag agc att-3') and MKK7-D1 reverse primer (SEQ. ID. NO: 20), MKK7-D5 forward primer (SEQ. ID. NO: 33: 5'-cg gga tcc gcc ggc tgt gcc gcc tac-3'), MKK7-D5 reverse primer (SEQ. ID. NO: 20), MKK7-D6 forward primer (SEQ. ID. NO: 19), MKK7-D6 reverse primer (SEQ. ID. NO: 34: 5'-at agt tta gcg gc cg cta aat gcg ctc ggg gat ggg-3') were used to perform PCR. As shown in FIG. 13A, full length MKK7 was divided into 3 fragments, D1, D5 and D6, and by using the primer mentioned above, they were amplified and inserted into pGST expression vector.

In order to over-express the vectors that express MKK7 fragments of D1, D5 and D6, 3X106 HEK293T cell line was planted in 100 mm culture dish and the cloned MKK7 D1, D5 and D6 fragment expression vectors were transfected into the cell line by using Lipofectamine LTX reagent. The cell lysate was extracted from the transfected cell and GST-Pull down analysis was performed. The GST-pull down analysis was performed as the method mentioned above.

As the result, as shown in FIG. 13B, the binding fragments of MKK7 against TIP41 were full length MKK protein and fragment D6. Consequently, it was identified that TIP41 binds into N terminal region with 1-85 amino acid sequence of MKK7 (SEQ. ID. NO: 35) (FIG. 13B).

EXAMPLE 15

Apoptosis Mediated by MKK7/JNK Pathway

<15-1> Decrease of Apoptosis by MKK7 Depletion

In order to identify that apoptosis tolerance is mediated by the interaction between MKK7 and TIPP41, the decrease of apoptosis tolerance by siRNA against MKK7 was examined.

siRNA against TIP41, and MKK7 and mixture of both were introduced into Huh7 liver cancer cell, and, once stimulating cells with 100 ng/ml TRAIL for about 0, 3 and 6 hours, then apoptosis was measured using FACS analysis with Annexin V-FITc/PI staining method.

As the result, MKK7 knockdown reduced apoptosis by TIP41 depletion and TRAIL treatment. Consequently, the important role of MKK7 in apoptosis induced by TIP41 protein repression and TRAIL treatment was identified (FIG. 14A).

<15-2> Activation of MKK7/JNK Pathway by TIP41 Depletion

In order to identify if depletion of TIP41 influences activation of MKK7 directly, and its influence on MKK7 signal transduction, in vitro immune-co-kinase analysis was performed. Immune-co-kinase analysis is a type of immunoprecipitation; it is an experiment method that identifies the level of phosphorylation by precipitating MKK7 and then quantitatively adding substrates of MKK7 and substrates that influence MKK signal transduction in vitro. After using MKK7 antibody as mentioned above for immunoprecipitation, Protein G bead with MKK7 protein bound was acquired, and afterwards recombination GST-JNK1, a substrate of MKK7, and GST-c-Jun, a substrate of JNK1, and marker isotope (−32P) were added into kinase buffer and reacted for about 30 minutes at about 37° C. Afterwards, 1× protein loading dye was added, and was boiled for about 5 minutes at about 95° C. After electrophoresis in 10% SDS-PAGE gel, the gel was dried in gel dryer, and then was photosensitized with BAS reader (radiation measuring instrument, Fujitsu, Japan).

FIG. 14B shows that MKK7 was activated by depletion of TIP41 and phosphorylated GST-JNK1, a substrate of MKK7, and the activated JNK1 phosphorylated GST-c-jun protein, a substrate of JNK pathway. Therefore, it was proved that TIP41 protein depletion and TRAIL treatment activates MKK7, and JNK transduction pathway is activated through this (FIG. 14B).

Production examples are provided for the compositions of the present invention as follows.

FORMULATION EXAMPLE 1

Preparation of a Pharmaceutical Preparation

<1-1> Preparation of Powders
Inhibitor for expression or activation of TIP41 protein 2 g
Lactose 1 g
The above ingredients were mixed and filled in a airtight pouch to prepare a powder formulation.

<1-2> Preparation of a Tablet
Inhibitor for expression or activation of TIP41 protein 100 mg
Corn starch 100 mg
Lactose 100 mg
Magnesium stearate 2 mg
The above ingredients were mixed and then tabletted according to a conventional preparation method to prepare a tablet formulation.

<1-3> Preparation of a Capsule
Inhibitor for expression or activation of TIP41 protein 100 mg
Corn starch 100 mg
Lactose 100 mg
Magnesium stearate 2 mg
The above ingredients were mixed, and then sealed in a gelatin capsule according to a conventional preparation method of tablets to prepare a capsule formulation.

<1-4> Preparation of Pill
Inhibitor for expression or activation of TIP41 protein 1 g
Lactose 1.5 g
Glycerin 1 g
Xylitol 0.5 g
The above ingredients were mixed and prepared into a pill according to a conventional method in such a manner that one pill has a weight of 4 g.

<1-5> Preparation of Granules
Inhibitor for expression or activation of TIP41 protein 150 mg
Soybean extracts 50 mg
Glucose 200 mg
Starch 600 mg
The above ingredients were mixed and 100 mg of 30% ethanol was added thereto, followed by drying at 60° C. After formation of granules, the granules were filled into packaging.

INDUSTRIAL APPLICABILITY

As explained above, when the liver cancer cell lines showing resistance to TRAIL are treated with TIP41 siRNA to inhibit expressions and then, treated with TRAIL, a specific apoptosis of cancer cell lines is induced. The same effect is found in cases of not only liver cancer but lung cancer and colon cancer having resistance against TRAIL. In addition, when a mouse receives a transplantation of cancer cells and is administered with TIP41 siRNA and TRAIL, the size of cancer cells is reduced and apoptosis of cancer cells is induced. Based on the effect shown above, the composition of the present invention including inhibitors for expression, or activity of TIP41 may be used for increasing TRAIL sensitivity or for the prevention and treatment of cancer as an anti-cancer adjuvant.

What is claimed is:

1. A method for enhancing sensitivity of cancer to TNF Related Apoptosis Inducing Ligand (TRAIL), comprising a step of administering a pharmaceutically effective amount of a TOR Signaling Pathway Regulator-Like (TIP41) expression inhibitor or a TIP41 activity inhibitor into a subject with TRAIL-resistance-related disease, wherein the TIP41 expression inhibitor or TIP41 activity inhibitor is a nucleic acid that binds to TIP41.

2. The method of claim 1, wherein the related TRAIL-resistance-related disease is cancer, inflammatory disease or autoimmune disease.

3. The method of claim 2, wherein the cancer is selected from the group consisting of liver cancer, colon cancer, cervical cancer, kidney cancer, stomach cancer, prostate cancer, breast cancer, brain tumor, lung cancer, uterine cancer, bladder cancer, blood cancer and pancreatic cancer.

4. The method of claim 2, wherein the inflammatory disease is selected from the group consisting of dermatitis, allergy, atopy, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, Rheumatic fever, systemic lupus erythematosus, fibromyalgia, psoriatic arthritis, degenerative arthritis, rheumatoid arthritis, shoulder joint arthritis, tendinitis, tendonitis, tenosynovitis, peritendinitis, myositis, hepatitis, cystitis, nephritis, sjogren's syndrome, multiple sclerosis, and acute and chronic inflammation.

5. The method of claim 2, wherein the autoimmune disease is selected from the group consisting of rheumatoid arthritis, multiple sclerosis, Myasthenia gravis, Graves disease, Hashimoto's throiditis, Addison's disease, vitiligo, systemic sclerosis, Goodpasture syndrome, Becet's disease, Crohn's disease, ankylosing spondylitis, uveitis, thrombocytopenic purpura, Pemphigus vulgaris, Diabetes, Autoimmune Anemia, cryoglobulinemia, adrenoleukodystrophy (ALD), and systemic lupus erythematosus (SLE).

6. The method of claim 1, wherein the TIP41 expression inhibitor is selected from the group consisting of an antisense nucleotide, a short interfering RNA, a short hairpin RNA, and an aptamer, capable of suppressing TIP41 expression.

7. The method of claim 1, wherein the TIP41 has an amino acid sequence of SEQ ID NO: 1.

8. A method for treatment of a TNF Related Apoptosis Inducing Ligand (TRAIL)-resistant cancer, comprising a step of administering a pharmaceutically effective amount of a TOR Signaling Pathway Regulator-Like (TIP41) expression inhibitor or a TIP41 activity inhibitor in combination with TRAIL, simultaneously, separately, or sequentially into a subject in need thereof, wherein the TIP41 expression inhibitor or TIP41 activity inhibitor is a nucleic acid that binds to TIP41.

9. The method of claim 8, wherein the TIP41 has an amino acid sequence of SEQ ID NO: 1.

10. The method of claim 8, wherein the TIP41 expression inhibitor is selected from the group consisting of an antisense nucleotide, a short interfering RNA, a short hairpin RNA, and an aptamer, capable of suppressing TIP41 expression.

11. The method of claim 8, wherein the cancer is selected from the group consisting of liver cancer, colon cancer, cervical cancer, kidney cancer, stomach cancer, prostate cancer, breast cancer, brain tumor, lung cancer, uterine cancer, bladder cancer, blood cancer and pancreatic cancer.

\* \* \* \* \*